US009758786B2

(12) United States Patent
Trieu

(10) Patent No.: US 9,758,786 B2
(45) Date of Patent: Sep. 12, 2017

(54) COMPOSITIONS AND METHODS FOR TREATING PANCREATIC CANCER

(71) Applicant: Autotelic LLC, City of Industry, CA (US)

(72) Inventor: Vuong Trieu, Agoura Hills, CA (US)

(73) Assignee: AUTOTELIC, LLC, City of Industry ( * ) Notice: Subject to any disclaimer, the term of this patent is extended or adjusted under 35 U.S.C. 154(b) by 0 days.

(21) Appl. No.: 15/019,819

(22) Filed: Feb. 9, 2016

(65) Prior Publication Data
US 2017/0226517 A1    Aug. 10, 2017

(51) Int. Cl.
A61K 48/00        (2006.01)
C12N 15/113       (2010.01)
A61K 31/7088      (2006.01)
A61K 9/00         (2006.01)
A61K 31/513       (2006.01)
A61K 31/495       (2006.01)
A61K 31/519       (2006.01)
A61K 31/282       (2006.01)
A61K 31/337       (2006.01)
A61K 31/407       (2006.01)
A61K 31/7068      (2006.01)
A61K 31/7125      (2006.01)

(52) U.S. Cl.
CPC ........ C12N 15/1136 (2013.01); A61K 9/0019 (2013.01); A61K 31/282 (2013.01); A61K 31/337 (2013.01); A61K 31/407 (2013.01); A61K 31/495 (2013.01); A61K 31/513 (2013.01); A61K 31/519 (2013.01); A61K 31/7068 (2013.01); A61K 31/7088 (2013.01); A61K 31/7125 (2013.01); C12N 2310/11 (2013.01); C12N 2310/315 (2013.01); C12N 2320/31 (2013.01); C12N 2320/32 (2013.01); C12N 2320/35 (2013.01)

(58) Field of Classification Search
CPC .................................................... A61K 48/00
See application file for complete search history.

(56) References Cited

U.S. PATENT DOCUMENTS

| | | |
|---|---|---|
| 4,699,615 A | 10/1987 | Fischell et al. |
| 4,999,339 A | 3/1991 | Paradise et al. |
| 5,221,620 A | 6/1993 | Purchio et al. |
| 5,369,527 A | 11/1994 | McCracken |
| 5,464,945 A | 11/1995 | Reynolds et al. |
| 5,525,468 A | 6/1996 | McSwiggen |
| 5,550,316 A | 8/1996 | Mintz |
| 5,571,714 A | 11/1996 | Dasch et al. |
| 5,596,072 A | 1/1997 | Culpepper et al. |
| 5,683,902 A | 11/1997 | Hampel et al. |
| 5,733,523 A | 3/1998 | Kuijpers et al. |
| 5,801,154 A | 9/1998 | Baracchini et al. |
| 5,843,150 A | 12/1998 | Dreessen et al. |
| 5,843,974 A | 12/1998 | Swift |
| 5,948,888 A | 9/1999 | de la Monte et al. |
| 5,958,769 A | 9/1999 | Roberts et al. |
| 6,045,802 A | 4/2000 | Schlom et al. |
| 6,094,598 A | 7/2000 | Elsberry et al. |
| 6,120,763 A | 9/2000 | Fakhrai et al. |
| 6,153,388 A | 11/2000 | Reintgen |
| 6,248,723 B1 | 6/2001 | Irvin |
| 6,376,199 B1 | 4/2002 | Caniggia et al. |
| 6,432,452 B1 | 8/2002 | Aylward |
| 6,436,909 B1 | 8/2002 | Dean et al. |
| 6,455,689 B1 | 9/2002 | Schlingensiepen et al. |
| 6,468,986 B1 | 10/2002 | Zuckermann et al. |
| 6,471,689 B1 | 10/2002 | Joseph et al. |
| 6,503,242 B1 | 1/2003 | Elsberry |
| 6,764,472 B1 | 7/2004 | Burke et al. |
| 6,900,299 B1 | 5/2005 | Mohapatra et al. |
| 6,972,171 B1 | 12/2005 | Schlingensiepen et al. |
| 7,101,543 B2 | 9/2006 | Fakhrai |
| 7,563,778 B2 | 7/2009 | Schlingensiepen et al. |
| 7,667,027 B2 | 2/2010 | Schlingensiepen et al. |
| 8,097,597 B2 | 1/2012 | Schlingensiepen et al. |
| 8,177,775 B2 | 5/2012 | Kunst |
| 8,476,246 B2 | 7/2013 | Schlingensiepen et al. |
| 8,629,117 B2 | 1/2014 | Schlingensiepen et al. |
| 8,822,425 B2 | 9/2014 | Schlingensiepen et al. |
| 9,375,435 B2 | 6/2016 | Walther et al. |

(Continued)

FOREIGN PATENT DOCUMENTS

DE    199 12 434 A1    9/2000
EP    0 293 785 A2    12/1988

(Continued)

OTHER PUBLICATIONS

Bogdahn et al. Autocrine stimulation of malignant gliomas in vitro by TGF-beta. A Study with phsophorothioate antisense oligonucleotides. Proceedings of the American Association for Cancer Research (1993). 34:518.

Efimov et al. Synthesis of polyethylele glycol-oligonucleotide conjugates. Bioorganiceskaa Khimia (1993). 19 (8):800-804.

Jansen et al. Antisense therapy for cancer—the time of truth. Lancet Oncol (2002). 3(11):672-683.

Jaschke, A. Oligonucleotide-Poly(ethylene glycol) Conjugates: Synthesis, Properties, and Applications. ACS Symposium Series (1997). 680(1):265-283.

Mahato et al. Modulation of gene expression by antisense and antigene oligodeoxynucleotides and small interfering RNA. Expert Opin Drug Deliv (2005). 2(1):3-28.

PCT/EP94/01362 International Search Report dated Nov. 8, 1994; 4 pages (Family 1).

(Continued)

Primary Examiner — Kimberly Chong
(74) Attorney, Agent, or Firm — Hema Vakharia-Rao; Nixon Peabody LLP

(57) ABSTRACT

Provided herein are composition for sensitizing tumors to anti-tumor therapies. The compositions include antisense oligonucleotides against TGFβ2, wherein the compositions sensitize tumors to anti-tumor therapies. Also provided herein are method for treating cancer using the compositions described herein.

7 Claims, 2 Drawing Sheets

(56) References Cited

U.S. PATENT DOCUMENTS

| | | | |
|---|---|---|---|
| 2002/0086812 A1* | 7/2002 | Schweinfest | C07K 14/4702 514/1 |
| 2002/0165174 A1 | 11/2002 | Gill et al. | |
| 2003/0040499 A1 | 2/2003 | Sclingensiepen et al. | |
| 2003/0171738 A1 | 9/2003 | Konieczynski et al. | |
| 2003/0186906 A1 | 10/2003 | Schlingensiepen et al. | |
| 2003/0215489 A1* | 11/2003 | Kasid | A61K 9/1272 424/450 |
| 2004/0006030 A1 | 1/2004 | Monia et al. | |
| 2005/0272644 A1 | 12/2005 | Chung | |
| 2006/0015952 A1 | 1/2006 | Filvaroff | |
| 2007/0155685 A1 | 7/2007 | Schlingensiepen et al. | |
| 2007/0196269 A1 | 8/2007 | Schlingensiepen et al. | |
| 2010/0160208 A1 | 6/2010 | Schlingensiepen et al. | |
| 2010/0286236 A1 | 11/2010 | Schlingensiepen et al. | |
| 2011/0024929 A1 | 2/2011 | Nakamura et al. | |
| 2011/0136893 A1 | 6/2011 | Schlingensiepen et al. | |

FOREIGN PATENT DOCUMENTS

| | | |
|---|---|---|
| EP | 0 433 225 A1 | 6/1991 |
| EP | 0 542 679 A1 | 5/1993 |
| EP | 0 502 036 B1 | 12/1995 |
| EP | 1 008 649 A2 | 6/2000 |
| EP | 1 133 988 A1 | 9/2001 |
| EP | 1992360 A1 | 11/2008 |
| EP | 2248895 A2 | 11/2010 |
| EP | 2 453 017 A1 | 5/2012 |
| WO | WO 90/10030 A1 | 9/1990 |
| WO | WO 93/07883 A1 | 4/1993 |
| WO | WO 94/25588 A2 | 11/1994 |
| WO | WO 94/29452 A2 | 12/1994 |
| WO | WO 95/00103 A2 | 1/1995 |
| WO | WO 95/02051 A2 | 1/1995 |
| WO | WO 95/02422 A1 | 1/1995 |
| WO | WO 95/05864 A1 | 3/1995 |
| WO | WO 95/17507 A1 | 6/1995 |
| WO | WO 96/02143 A1 | 2/1996 |
| WO | WO 96/23065 A2 | 8/1996 |
| WO | WO 96/31600 A1 | 10/1996 |
| WO | WO 96/39415 A1 | 12/1996 |
| WO | WO 97/39120 A2 | 10/1997 |
| WO | WO 98/33904 A2 | 8/1998 |
| WO | WO 99/50411 A2 | 10/1999 |
| WO | WO 99/63975 A2 | 12/1999 |
| WO | WO 00/01410 A1 | 1/2000 |
| WO | WO 01/68122 A2 | 9/2001 |
| WO | WO 01/68146 A2 | 9/2001 |
| WO | WO 02/02132 A1 | 1/2002 |
| WO | WO 03/033701 A1 | 4/2003 |
| WO | WO 03/064457 A1 | 8/2003 |
| WO | WO 2004/005552 A1 | 1/2004 |
| WO | WO 2004/047742 A2 | 6/2004 |
| WO | WO 2004/060300 A2 | 7/2004 |
| WO | WO 2004/093945 A1 | 11/2004 |
| WO | WO 2004/104197 A1 | 12/2004 |
| WO | WO 2005/014812 A2 | 2/2005 |
| WO | WO 2005/059133 A2 | 6/2005 |
| WO | WO 2005/084712 A2 | 9/2005 |
| WO | WO 2006/117400 A2 | 11/2006 |
| WO | WO 2008/077956 A2 | 7/2008 |
| WO | WO 2010/055148 A2 | 5/2010 |
| WO | WO 2011/012713 A1 | 2/2011 |
| WO | WO 2011/154542 A1 | 12/2011 |
| WO | 2013078286 A1 | 5/2013 |
| WO | WO 2014/154835 A2 | 10/2014 |
| WO | WO 2015/140150 A1 | 9/2015 |

OTHER PUBLICATIONS

PCT/EP9/00497 International Search Report dated Mar. 24, 1999; 10 pages (Family 2).
PCT/EP99/04013 International Search Report dated May 17, 2000; 6 pages (Family 3).
PCT/EP01/02694 International Search Report dated Oct. 31, 2001; 3 pages (Family 4).
PCT/EP2004/004211 International Search Report dated Sep. 21, 2004; 5 pages (Family 5).
PCT/EP2004/053604 International Search Report and Written Opinion dated Jan. 30, 2006; 16 pages (Family 6).
PCT/EP2004/053604 International Preliminary Report on Patentability dated Jun. 20, 2006; 10 pages (Family 6).
PCT/EP2006/062067 International Search Report and Written Opinion dated Jan. 27, 2006; 14 pages (Family 7).
PCT/EP2006/062067 International Preliminary Report on Patentability dated Aug. 6, 2007; 9 pages (Family 7).
PCT/EP2007/064494 International Search Report and Written Opinion dated Sep. 9, 2008; 10 pages (Family 8).
PCT/EP2007/064494 International Preliminary Report on Patentability dated Jun. 24, 2009; 7 pages (Family 8).
PCT/EP2009/065179 International Search Report and Written Opinion dated Jun. 16, 2010; 15 pages (Family 9).
PCT/EP2009/065179 International Preliminary Report on Patentability dated May 17, 2011; 8 pages (Family 9).
PCT/EP2010/061152 International Search Report and Written Opinion dated Oct. 27, 2010; 13 pages (Family 10).
PCT/EP2010/061152 International Preliminary Report on Patentability dated Jan. 31, 2013; 7 pages (Family 10).
PCT/EP2011/059744 International Search Report and Written Opinion dated Sep. 5, 2011; 10 pages (Family 11).
PCT/EP2011/059744 International Preliminary Report on Patentability dated Dec. 14, 2012; 6 pages (Family 11).
PCT/EP2005/002101 International Search Report and Written Opinion dated Oct. 4, 2006; 18 pages (Family 12).
PCT/EP2005/002101 International Preliminary Report on Patentability dated Nov. 7, 2006; 12 pages (Family 12).
Arteaga et al. Reversal of tamoxifen resistance of human breast carcinomas in vivo by neutralizing antibodies to transforming growth factor-beta. J Natl Cancer Inst (1999). 91(1):46-53.
Agrawal, S. Antisense oligonucleotides: towards clinical trials. Trends Biotechnol (1996). 14(10)376-387.
Agrawal et al. Antisense therapeutics: is it as simple as complementary base recognition? Mol Med Today (2000). 6(2):72-81.
Akporiage et al. Concomitant Expression of Interferon-γ and Antisense TGF-β Transgenes Enhances the Immunogenicity of a Murine Mammary Carcinoma Cancer Gene Therapy (1997). 4(6): P-150. Abstract Only.
Behl et al. Transforming Growth Factor-62 -antisense-oligonucleotides inhibit a human melanoma cell line under serum-enriched and stimulate under serum-free culture conditions. Proceedings of the 82$^{nd}$ Annual Meeting of the American Association for Cancer Research (1991). Abstract Only.
Bellone et al. Differential expression of transforming growth factors-β1, -β2 and -β3 in human colon carcinoma. Eur J Cancer (2001). 37:224-233.
Bodmer et al. Immunosuppression and Transforming Growth Factor-β in Glioblastoma. J Immunol (1989). 143(10):3222-3229.
Bogdahn et al. Targeted therapy for high-grade glioma with the TGF-β2 inhibitor trabedersen: results of a randomized and controlled phase IIb study. Neuro Oncol (2011). 13(1):132-142.
Bonora, GM. Polymer-Conjugated Bioactive Oligonucleotides Journal of Bioactive and Compatible Polymers (2002). 17(5)375-389.
Branch. A good antisense molecule is hard to find. Trends Biochem Sci (1998). 23(2):45-50.
Brossalina et al. Triplex-forming oligonucleotides trigger conformation changes of a target hairpin sequence. Nucleic Acids Res (1996). 24(17):3392-3398.
Chai et al. Specific Transforming Growth Factor-β Subtypes Regulate Embryonic Mouse Meckel's Cartilage and Tooth Development. Developmental Biology (1994). 162:85-103.
Chirila et al. The use of synthetic polymers for delivery of therapeutic antisense oligodeoxynucleotides. Biomaterials (2002). 23(2):321-342.
Crook, S.T. Therapeutic Application of Oligonucleotides. Annu Rev Pharmacol Toxicol (1992). 32:329-376.

(56) References Cited

OTHER PUBLICATIONS

Crook, S.T (Ed.) "Basic Principles of Antisense Therapeutics" Antisense Research Application. Chapter 1, pp. 1-50. Springer-Verlag (1998).
Crystal, R. Transfer of genes to humans: early lessons and obstacles to success. Science (1995). 270(5235):404-410.
De Martin et al. Complementary DNA for human glioblastoma-derived T cell suppressor factor, a novel member of the transforming growth factor-beta gene family. EMBO J (1987). 6(12):3673-3677.
Efimov et al. Dipentafluorophenyl carbonate—a reagent for the synthesis of oligonucleotides and their conjugates. Nucleic Acids Res (1993). 21(23):5337-5344.
Ehrlich et al. Use of partially phosphorothioated "antisense" oligodeoxynucleotides for sequence-dependent modulation of hematopoiesis in culture. Antisense Res Dev (1994) 4(3):173-83.
Fakhrai et al. Eradication of established intracranial rat gliomas by transforming growth factor beta antisense gene therapy. Proc Natl Acad Sci USA (1996). 93(7):2909-2914.
Ficht et al. Single-nucleotide-specific PNA-peptide ligation on synthetic and PCR DNA templates. J Am Chem Soc (2004). 126(32):9970-9981.
Fitzpatrick et al. Transforming growth factor-beta: antisense RNA-mediated inhibition affects anchorage-independent growth, tumorigenicity and tumor-infiltrating T-cells in malignant mesothelioma. Growth Factors (1994). 11(1):29-44.
Fitzpatrick et al. Antisense oligonucleotides specific for transforming growth factor beta2 inhibit the growth of malignant mesothelioma both in vitro and in vivo. Cancer Res (1997). 57(15):3200-3207.
Freireich et al. Quantitative Comparison of Toxicity of Anitcancer Agents in Mouse, Rat, Hamster, Dog, Monkey, and Man. Cancer Chemotherapy Reports (1966). 50(4):219-244.
Friedmann, T. Overcoming the obstacles to gene therapy. Sci Am (1997). 276(6):96-101.
Hatzfeld et al. Release of Early Human Hematopoietic Progenitors from Quiescence by Antisense Transforming Growth Factor β1 or Rb Oligonucleotides. Journal of Experimental Medicine (1991). 174:925-929.
Hau et al. Inhibition of TGF-beta2 with AP 12009 in recurrent malignant gliomas: from preclinical to phase I/II studies. Oligonucleotides (2007). 17(2):201-212.
Hauschild et al. Results of a phase III, randomized, placebo-controlled study of sorafenib in combination with carboplatin and paclitaxel as second-line treatment in patients with unresectable stage III or stage IV melanoma. J Clin Oncol (2009). 27(17):2823-2830.
Hirsch et al. In vitro restoration of T cell responses in tuberculosis and augmentation of monocyte effector function against Mycobacterium tuberculosis by natural inhibitors of transforming growth factor β. Proc Natl Acad Sci USA (1997). 94(8):3926-3931.
Hodi et al. Improved survival with ipilimumab in patients with metastatic melanoma. N Engl J Med (2010). 363(8):711-723.
Huang et al. Transforming growth factor beta 1 (TGF beta 1) is an autocrine positive regulator of colon carcinoma U9 cells in vivo as shown by transfection of a TGF beta 1 antisense expression plasmid. Cell Growth Differ (1995). 6(12):1635-1642.
Inagaki et al. Cell physiology of antisense TGF-beta oligomers in hepatoma cells. Ann NY Acad Sci (1992). 660(1):315-317.
Inagaki et al. Antisense oligonucleotides: inhibition of liver cell proliferation and in vivo disposition. Transplant Proc (1992). 24(6):2971-2972.
Jachimczak et al. TGF-β-Phosphorothioate-Antisense-Oligonucleotides may reverse immunosuppressive effects of TGF-β in malignant gliomas in vitro. Proceedings of the 82nd Annual Meeting of the American Association for Cancer Research (1991). Abstract Only.
Jachimczak et al. The effect of transforming growth factor-β2-specific phosphorothioate-anti-sense oligodeoxynucleotides in reversing ceullar immunosuppression in malignant glioma. J Neurosurg (1993). 78:944-951.
Jachimczak et al. Transforming growth factor-beta-mediated autocrine growth regulation of gliomas as detected with phosphorothioate antisense oligonucleotides. Int J Cancer (1996). 65(3):332-337.
Jaschke et al. Synthesis and Properties of Oligodeoxyribonucleotide—Polyethyleneglycol Conjugates. Nucleic Acids Res (1994). 22(22):4810-4817.
Jaschinski et at (530) Activity of the TGF-beta 2 specific antisense oligodeoxynucleotide trabedersen in an orthotopic xonograft mouse model of metastatic pancreatic cancer. Eur J Cancer Suppl (2010). 8(7):169.
Jaschinski et at (359) Effect of the TGF-beta 2 specific antisense oligodeoxynucleotide trabedersen on TGF-beta 2 and -beta 1 expression in human glioma cells: Cross-regulatory loops regulate TGF-beta isoform expression. Eur J Cancer Suppl (2010). 8(7):113-114.
Jennings et al. Comparison of the Biological Actions of TGF-β1 and TGF-β2: Differential Activity in Endothelial Cells. J Cell Physiol (1988):137:167-172.
Kingsley, D.M. The TGF-beta superfamily: new members, new receptors, and new genetic tests of function in different organisms. Genes Dev (1994). 8(2):133-146.
Lu et at Chemical strategies for the synthesis of peptide-oligonucleotide conjugates. Bioconjug Chem (2010). 21(2):187-202.
Lafyatis et al. Sequence specific protein binding to and activation of the TGF-β3 promoter through a repeated TCCC motif. Nucleic Acids Research (1991). 19(23):6419-6425.
Lennox et at Chemical modification and design of anti-miRNA oligonucleotides Gene Therapy (2011). 18:111-1120.
Lorusso et al. A phase II study of gemcitabine in patients with transitional cell carcinoma of the urinary tract previously treated with platinum. Italian Co-operative Group on Bladder Cancer. Eur J Cancer (1998). 34(8):1208-1212.
Maher et al. Specific hybridization arrest of dihydrofolate reductase mRNA in vitro using anti-sense RNA or anti-sense oligonucleotides. Arch Biochem Biophys (1987). 253(1):214-220.
Marzo et al. Antisense oligonucleotides specific for transforming growth factor beta2 inhibit the growth of malignant mesothelioma both in vitro and in vivo. Cancer Res (1997). 57(15):3200-3207.
Maxwell et al. Effect of the expression of transforming growth factor-β2 in primary human glioblastomas on immunosuppression and loss of immune surveillance. J Neurosurg (1992). 76:799-804.
Milner et at Selecting effective antisense reagents on combinatorial oligonucleotide arrays. Nat Biotechnol (1997). 15(6):537-541.
Monia et al. Nuclease resistance and antisense activity of modified oligonucleotides targeted to Ha-ras. J Biol Chem (1996). 271(24):14533-14540.
Morris et al. Phase I study of GC1008 (fresolimumab). A human anti-transforming growth factor-beta (TGFβ) monoclonal antibody in patients with advanced malignant melanoma or renal cell carcinoma. PLoS One (2010). 9(3):e90353.
No Author. Equivalent Surface Area Dosage Conversion Factors. Retrieved from: http://ncifrederick.cancer/gov/Lasp/Acuc/Frederick/Media/Documents/ACUC42.pclf (2012); 1 page.
Opalinska et al. Nucleic-acid therapeutics: basic principles and recent applications. Nat Rev Drug Discov (2002). 1(7):503-514.
Oettle et al. Trabedersen (AP12009) in the treatment of pancreatic carcinoma and other malignant tumors: interim results of the Pbase I/II study. Eur J Cancer Suppl (2009). 7(2):138.
Oettle et al. Final results of a phase I/II study in patients with pancreatic cancer, malignant melanoma, and colorectal carcinoma with trabedersen. J Clin Oncol (2012) 30:2 pages Abstract Only.
Palu et al. In pursuit of new developments for gene therapy of human diseases. J Biotechnol (1999). 68(1):1-13.
Park et al. Expression of an antisense transforming growth factor-beta1 transgene reduces tumorigenicity of EMT6 mammary tumor cells. Cancer Gene Therapy (1997). 4(1):42-50.
Pelzer et al. Best supportive care (BSC) versus oxaliplatin, folinic acid and 5-fluorouracil (OFF) plus BSC in patients for second-line advanced pancreatic cancer: a phase III-study from the German CONKO-study group. Eur J Cancer (2011). 47(11):1676-1681.
Peracchi, A. Prospects for antiviral ribozymes and deoxyribozymes. Rev Med Virol (2004). 14(1):47-64.

(56) References Cited

OTHER PUBLICATIONS

Picon et al. A subset of metastatic human colon cancers expresses elevated levels of transforming growth factor beta1. Cancer Epidemiol Biomarkers Prev (1998). 7(6):497-504.
Pisetsky et al.Stimulation of in vitro proliferation of murine lymphocytes by synthetic oligodeoxynucleotides. Mol Biol Rep (1993). 18(3):217-221.
Potts et al. Epithelial-mesenchymal transformation of embryonic cardiac endothelial cells is inhibited by a modified antisense oligodeoxynucleotide to transforming growth factor β3. Proc Natl Acad Sci USA (1991). 88:1516-1520.
Probst et al. The G-tetrad in antisense targeting. Trends Genet (1996). 12(8):290-291.
Reed et al. BCL2-mediated tumorigenicity of a human T-lymphoid cell line: synergy with MUC and inhibition by BCL2 antisense. Proc Natl Acad Sci USA (1990). 87(10):3660-3664.
Reed et al. Expression of transforming growth factor-beta 2 in malignant melanoma correlates with the depth of tumor invasion. Implications for tumor progression. Am J Pathol (1994). 145(1):97-104.
Remick et al. Novel oral combination chemotherapy in the treatment of intermediate-grade and high-grade AIDS-related non-Hodgkin's lymphoma. J Clin Oncol (1993). 11(9):1691-1702.
Roberts et al. Transforming group factor type β: Rapid induction of fibrosis and angiogenesis in vivo and stimulation of collagen formation in vitro. PNAS (1986). 83:4167-4171.
Roth et at Chemotherapy and immunotherapy of malignant glioma: molecular mechanisms and clinical perspectives. Cell Mol Life Sci (1999). 56(5-6):481-506.
Rubenstein et al Inhibition of PC-3 prostate cancer cell growth in vitro using both antisense oligonucleotides and taxol. Med Oncol (2003). 20(1):29-35.
Scherer et al. Approaches for the sequence-specific knockdown of mRNA. Nat Biotechnol (2003). 21(12) 1457-1465.
Schlingensiepen et al. Intracerebral and intrathecal infusion of the TGF-beta 2-specific antisense phosphorothioate oligonucleotide AP 12009 in rabbits and primates: toxicology and safety. Oligonucleotides (2005). 15(2):94-104.
Schlingensiepen et al. Targeted tumor therapy with the TGF-beta 2 antisense compound AP 12009. Cytokine Growth Factor Rev (2006). 17(1-2):129-139.
Schlingensiepen et al. Antisense therapeutics for tumor treatment: the TGF-beta2 inhibitor AP 12009 in clinical development against malignant tumors. Recent Results Cancer Res (2008). 177:137-150.
Singh et al. Recent developments in oligonucleotide conjugation. Chem Soc Rev (2010). 39(6):2054-2070.
Smetsers et al. Bias in Nucleotide Composition of Antisense Oligonucleotides. Antisense and Nucleic Acid Drug Development (1996). 6:63-67.
Spearman et al. Antisense oligodeoxyribonucleotide inhibition of TGF-beta 1 gene expression and alterations in the growth and malignant properties of mouse fibrosarcoma cells. Gene (1994). 149(1):25-29.
Stetsenko et at Efficient conjugation of peptides to oligonucleotides by "native ligation". J Org Chem (2000). 65(16):4900-4908.
Stull et al. Antigene, Ribozyme and Aptamer Nucleic Acid Dmgs: Progress and Prospects. Pharm Res (1995). 12(4):465-483.
Stull et al. Predicting antisense oligonucleotide inhibitory efficacy: a computational approach using histograms and thermodynamic indices. Nucleic Acids Res (1992). 20(13):3501-3508.
Tamm et al. Antisense therapy in oncology: new hope for an old idea? Lancet (2001). 358(9280):489-497.
Tanaka et al. Synthesis of oligoribonucleoties via phsphite-triester approach on a polymer support. Chem Pharm Bull (1986). 34:1426-1432.
Toulme et al. Antisense oligonucleotides: tools of molecular genetics and therapeutic agents. Ann Parasitol Hum Comp (1990). 65(Suppl 1):11-14.
Ueki et al. Excessive production of transforming growth-factor beta 1 can play an important role in the development of tumorigenesis by its action for angiogenesis: validity of neutralizing antibodies to block tumor growth. Biochim Biophys Acta (1992). 1137(2):189-196.
Vaerman et al. Antisense oligodeoxyribonucleotides suppress hematologic cell growth through stepwise release of deoxyribonucleotides. Blood (1997). 90(1):331-339.
Verma et al. Gene therapy—promises, problems and prospects. Nature (1997). 389(6648):239-242.
Von Hoff et al. Increased survival in pancreatic cancer with nab-paclitaxel plus gemcitabine. N Engl J Med (2013). 369(18):1697-1703.
Wojtowicz-Praga. Reversal of tumor-induced immunosuppression by TGF-beta inhibitors. Invest New Drugs (2003). 21(1):21-32.
Wojtowicz-Praga et al. Modulation of B16 melanoma growth and metastasis by anti-transforming growth factor beta antibody and interleukin-2 J Immunother Emphasis Tumor Immunol (1996). 19(3):169-175.
Wojtowicz-Praga, S. Reversal of tumor-induced immunosuppression: A new approach to cancer therapy. J Immunotherapy (1997). P165-177.
Wu et al. TGF-beta 1 is an autocrine-negative growth regulator of human colon carcinoma FET cells in vivo as revealed by transfection of an antisense expression vector. J Cell Biol (1992). 116(1):187-196.
Wu et al. Repression of autocrine transforming growth factor beta 1 and beta 2 in quiescent CBS colon carcinoma cells leads to progression of tumorigenic properties. Cell Growth Differ (1993). 4(2):115-123.
Yoo et al. A randomised phase II study of modified FOLFIRI.3 vs modified FOLFOX as second-line therapy in patients with gemcitabine-refractory advanced pancreatic cancer. Br J Cancer (2009). 101(10):1658-1663.
Yu et al. Hybrid oligonucleotides: synthesis, biophysical properties, stability studies, and biological activity. Bioorg Med Chem (1996). 4(10):1685-92.
Zhao et al. Effect of different chemically modified oligodeoxynucleotides on immune stimulation. Biochem Pharmacol (1996). 51(2):173-182.
Dawson, N.J. The Surface-Area/Body-Weight Relationship in Mice. Aust. J. Biol. Sci. (1967). 20:687-90.
PCT/US2016/017176 International Search Report and Written Opinion dated Sep. 16, 2016; 16 Pages.
PCT/US2016/017188 International Search Report and Written Opinion dated Sep. 16, 2016; 16 Pages.
Sagan et al., 51 Efficacy of Combined Treatment with Trabedersen and Decarbazine in Xenograft Mouse Model of Malignant Melanoma, European Journal of Cancer 2012, vol. 48(6), pp. 17-18 (Abstract Only).
Hwang et al., Treatment with Trabedersen- an anti-TGF-beta-2 antisense-primed Tumors to Subsequent Chemotherapies, European Journal of Cancer, 2016, pp. S1-S11(Abstract Only).

* cited by examiner

COMPOSITIONS AND METHODS FOR TREATING PANCREATIC CANCER

FIELD OF INVENTION

The invention relates to medicine and oncology. Provided herein are compositions and methods for treating cancers, including pancreatic cancer.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Pancreatic cancer is a devastating disease. It represents one of the worst solid tumors and has a diagnosis to mortality ratio approaching one. There are approximately 40,000 diagnoses per year in the US, and 350,000 diagnoses worldwide. Combinations of radiotherapy (RT), chemotherapy and surgery have been used to treat resectable, locally advanced unresectable, and metastatic cancer patients. However, the doses of treatments (e.g., RT and chemotherapy) are dictated by their associated toxicities. This in turn impacts the clinical efficacy of these treatments. There is an unmet need in the art for pancreatic cancer therapies and methods for treating same.

SUMMARY

The following embodiments and aspects thereof are described and illustrated in conjunction with compositions and methods which are meant to be exemplary and illustrative, not limiting in scope.

Provided herein are methods for sensitizing a tumor to antitumor therapies in a subject in need thereof. The methods comprise, consist of or consist essentially of providing a composition comprising an inhibitor of TGFβ signaling and administering an effective amount of the composition to the subject so as to sensitize the tumor.

Also provided herein are methods for treating, inhibiting, reducing the severity of and/or preventing metastasis of cancer in a subject in need thereof. The methods comprise, consist of or consist essentially of providing a composition comprising an inhibitor of TGFβ signaling and administering an effective amount of the composition to the subject so as to treat, inhibit, reduce the severity of and/or prevent metastasis of cancer in the subject.

In one embodiment of the methods described herein, the tumor is a pancreatic tumor.

In various embodiments, TGFβ signaling inhibitors include but are not limited to small molecules, antibodies or antigen-binding antibody fragments, intrabodies, aptamers, antisense oligonucleotides, RNA interference agents, and ribozymes.

In some embodiments, antibodies that may be used for TGFβ signaling inhibition for use in the methods described herein or in the compositions described herein include but are not limited to any one or more of Fresolimumad (GC-1008), Lerderlimumab (CAT-152), Metelimumab (CAT-162), or combinations thereof. In further embodiments, TGFβ signaling inhibitors for use in the methods described herein or in the compositions described herein include but are not limited to any one or more of PF-03446962 antibody (a fully-human monoclonal antibody against transforming growth-factor β (TGFβ) receptor ALK1), Galunisertib (LY2157299, a small molecule inhibitor of TGFβ signaling), Lucanix (an allogenic tumor vaccine comprising a mixture of four allogeneic human non-small cell lung cancer cell lines modified to express an antisense oligonucleotide targeting TGFβ2) or TGFβ2 antisense oligonucleotide in combination with GM-CSF, or combinations thereof. It is contemplated that any of these TGFβ signaling inhibitors set forth herein may be used in the methods described herein to treat pancreatic cancer alone or in combination with chemotherapeutic agents and/or radiation therapy as set forth herein.

In some embodiments, the inhibitor of TGFβ signaling is an antisense oligonucleotide specific for TGFβ2. In an embodiment, the antisense oligonucleotide specific for TGFβ2 is trabedersen or a variant, derivative or analog thereof.

In some embodiments, methods for treating, inhibiting, reducing the severity of or preventing metastasis of cancer in a subject in need thereof include first sensitizing the tumor using the TGFβ signaling inhibitor as set forth herein and subsequently administering exogenous therapeutic agents including chemotherapeutic agents, radiation therapy or a combination thereof.

In some embodiments, the inhibitor of TGFβ signaling sensitizes the tumor to subsequence therapies but does not or is not required to decrease the $IC_{50}$ of chemotherapeutic agents.

In various embodiments, trabedersen or a variant, derivative or analog thereof is administered prior to administration of cancer therapies such as chemotherapies or radiation therapy or a combination thereof. Administration of trabedersen or a variant, derivative or analog thereof in sufficient number of cycles as described herein prior to administration of cancer therapies in sensitizes the tumors to the cancer therapies.

DESCRIPTION OF THE INVENTION

Figure 1:
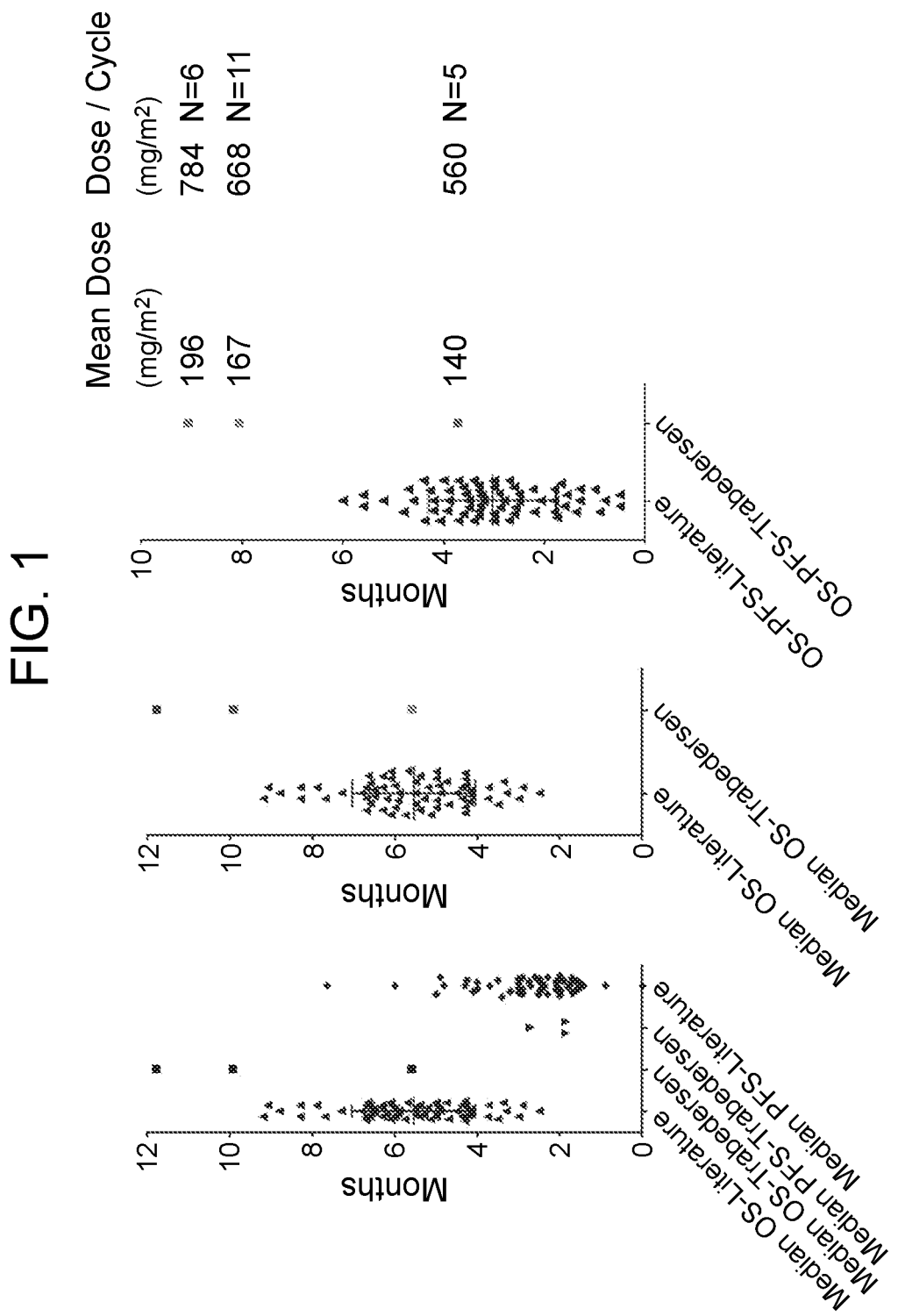
FIG. 1 depicts in accordance with various embodiments of the invention, the dose dependent increase in overall survival (OS) rate in pancreatic cancer patients when trabedersen is used as a second line treatment. OS and PFS of patients treated with trabedersen were compared to reported median OS and PFS. While PFS was not significantly different, the OS was higher than reported in the literature.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor N.Y., 2013); Kohler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

Definitions

In the event of any inconsistency with a term defined herein and those set forth in patents, published application and non-patent literature that are incorporated herein by reference, the definitions herein will control.

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of pancreatic cancer, delay or slowing of pancreatic cancer, and amelioration or palliation of symptoms associated with pancreatic cancer.

"Diseases", "conditions" and "disease conditions," as used herein may include, but are in no way limited to any form of malignant neoplastic cell proliferative disorders or diseases. Examples of such disorders include but are not limited to cancer and tumor.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant tumors, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. Melanoma is an invasive form of skin tumor. As used herein, the term "carcinoma" refers to a cancer arising from epithelial cells. Examples of cancer include, but are not limited to, nervous system tumor, brain tumor, nerve sheath tumor, breast cancer, colorectal cancer, colon cancer, rectal cancer, bowel cancer, carcinoma, lung cancer, hepatocellular cancer, gastric cancer, pancreatic cancer, cervical cancer, ovarian cancer, liver cancer, bladder cancer, cancer of the urinary tract, thyroid cancer, renal cancer, renal cell carcinoma, carcinoma, melanoma, head and neck cancer, brain cancer, and prostate cancer, including but not limited to androgen-dependent prostate cancer and androgen-independent prostate cancer. Examples of brain tumor include, but are not limited to, benign brain tumor, malignant brain tumor, primary brain tumor, secondary brain tumor, metastatic brain tumor, glioma, glioblastoma, glioblastoma multiforme (GBM), medulloblastoma, ependymoma, astrocytoma, pilocytic astrocytoma, oligodendroglioma, brainstem glioma, optic nerve glioma, mixed glioma such as oligoastrocytoma, low-grade glioma, high-grade glioma, supratentorial glioma, infratentorial glioma, pontine glioma, meningioma, pituitary adenoma, and nerve sheath tumor. Nervous system tumor or nervous system neoplasm refers to any tumor affecting the nervous system. A nervous system tumor can be a tumor in the central nervous system (CNS), in the peripheral nervous system (PNS), or in both CNS and PNS. Examples of nervous system tumor include but are not limited to brain tumor, nerve sheath tumor, and optic nerve glioma.

As used herein, the term "administering," refers to the placement of an agent or a composition as disclosed herein into a subject by a method or route which results in at least partial localization of the agents or composition at a desired site. "Route of administration" may refer to any administration pathway known in the art, including but not limited to oral, topical, aerosol, nasal, via inhalation, anal, intra-anal, peri-anal, transmucosal, transdermal, parenteral, enteral, or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the agent or composition may be in the form of solutions or suspensions for infusion or for injection, or as lyophilized powders. Via the enteral route, the agent or composition can be in the form of capsules, gel capsules, tablets, sugar-coated tablets, syrups, suspensions, solutions, powders, granules, emulsions, microspheres or nanospheres or lipid vesicles or polymer vesicles allowing controlled release. Via the topical route, the agent or composition can be in the form of aerosol, lotion, cream, gel, ointment, suspensions, solutions or emulsions. In an embodiment, agent or composition may be provided in a powder form and mixed with a liquid, such as water, to form a beverage. In accordance with the present invention, "administering" can be self-administering. For example, it is considered as "administering" that a subject consumes a composition as disclosed herein.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A "subject" can be one who has been previously diagnosed with or identified as suffering from or having a condition in need of treatment (e.g., pancreatic cancer) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

An "inhibitor" of TGFβ, as the term is used herein, can function in a competitive or non-competitive manner, and can function, in one embodiment, by interfering with the expression of the TGFβ protein. In one embodiment, the TGFβ protein is TGFβ2, having the sequence set forth in SEQ ID NO: 2 (NM_003238.3). Any of a number of different approaches can be taken to inhibit TGFβ (for example, TGFβ2) expression or activity. A TGFβ (for example, TGFβ2) inhibitor includes any chemical or biological entity that, upon treatment of a cell, results in inhibition of the biological activity caused by activation of TGFβ (for example, TGFβ2) in response to cellular signals. TGFβ (for example, TGFβ2) inhibitors, include, but are not limited to, small molecules, antibodies or antigen-binding antibody fragments, intrabodies, aptamers, antisense constructs, RNA interference agents, and ribozymes. In an exemplary embodiments, a small molecule inhibitor of TGFβ is a small molecule inhibitor of TGFβ receptor type I kinase (ALK5; an inhibitor is an ALK5 inhibitor). In another exemplary embodiment, an antibody inhibitor of TGFβ is a neutralizing anti-TGF-beta-1, -2, -3 antibody or TGF-beta binding fragments thereof or a neutralizing anti-TGF-beta receptor type I,-type II or type III antibody or TGF-beta receptors binding fragments thereof or a TGF trap. In a further exemplary embodiment, an inhibitor of TGFβ is an antisense oligonucleotide specific for mRNA encoding TGF-beta 1, -2, and -3 isotypes or other components of TGF-beta signaling assembly optionally comprising a modified nucleoside such as 2"-0, 4"-C-methylene linked bicyclic ribonucleotides, known as locked nucleic acids LNA (e.g., oxy-LNA, amino-LNA, thio-LNA), phosphorodiamidate morpholino oligomers (PMO), phosphorothioate (PS), 2"-0-methyl (2"-Ome), 2"-fluoro (2"-fluoro (2"-F), or 2"-methoxyethyl (2"-MOE) derivatives. In an additional exemplary embodiment, an inhibitor of TGFβ includes an antisense RNA molecule specific for TGF-beta2-mRNA like belagenpumatucel-L and/or TGF-beta1-mRNA or TGF-beta3-mRNA or other components of mRNA encoding TGF-beta signaling assembly. In a further exemplary embodiment, an inhibitor of TGFβ includes a silencing RNA molecule (siRNA) specific for mRNA encoding TGF-beta1, -2, and/or -3 isotypes or other components of TGF-beta signaling assembly. In an additional exemplary embodiment, an inhibitor of TGFβ includes a short hairpin RNA (shRNA) specific for mRNA encoding TGF-beta1, -2, and/or -3 isotypes or other components of TGF-beta signaling assembly. In an additional embodiment, an inhibitor of TGFβ includes a miRNA molecule specific for mRNA encoding TGF-beta1, -2, and/or -3 isotypes or other components of TGF-beta signaling assembly. In a further exemplary embodiment, an inhibitor of TGFβ includes an aptamer and/or spiegelmer molecule specific for TGF-beta1, -2, and/or -3 isotypes or other components of the TGF-beta signaling assembly. In a further exemplary embodiment, an inhibitor of TGFβ includes a ribozyme molecule specific for mRNA encoding TGF-beta1, -2, and/or -3 isotypes or other components of the TGF-beta signaling assembly. Antisense oligonucleotides (ASOs) are single-stranded polynucleotide molecules comprising 13-25 nucleotides, preferably 15-20 nucleotides, more preferred 15, 16, 17, 18, 19, 20, 21, 22 or 23 nucleotides, that hybridize to complementary RNA, inhibiting mRNA function, and preventing protein synthesis for example through accelerated mRNA degradation by RNase H or steric blockade. In some embodiments, the TGFβ2 inhibitor is an antisense oligonucleotide ASPH_0047 (from Isarna Therapeutics as described in WO2014/154835) which is a selective LNA-modified ASO gapmer targeting TGF-β2. In an embodiment, ASPH_0047 (ISTH0047) has the sequence 5'-CAAAGTATTTG-GTCTCC-3', as set forth in SEQ ID NO: 3.

In additional embodiments, TGFβ signaling inhibitors for use with the methods described herein include but are not limited to antisense oligonucleotides from Isarna Therapeutics as described in WO2014/154835 having the sequence CAAAGTATTTGGTCTCC (ASPH47; SEQ ID NO: 3), ACCTCCTTGGCGTAGTA (ASPH01; SEQ ID NO: 4), ACCTCCTTGGCGTAGTA (ASPH02; SEQ ID NO: 5), CCTCCTTGGCGTAGTA (ASPH03; SEQ ID NO: 6), CCTCCTTGGCGTAGTA (ASPH04; SEQ ID NO: 7), CTC-CTTGGCGTAGTA (ASPHOS; SEQ ID NO: 8), CTCCT-TGGCGTAGTA (ASPH06; SEQ ID NO: 9), CTCCTTG-GCGTAGTA (ASPH07; SEQ ID NO: 10), TCCTTGGCGTAGTA (ASPH08; SEQ ID NO: 11), CAGAAGTTGGCAT (ASPH09; SEQ ID NO: 12), CAGAAGTTGGCAT (ASPH10; SEQ ID NO: 13), CTGC-CCGCGGAT (ASPH15; SEQ ID NO: 14), TCTGC-CCGGAT (ASPH17; SEQ ID NO: 15), TCGCCTCGCAGGC (ASPH22; SEQ ID NO: 16), GGATCTGCCCGCGGA (ASPH26; SEQ ID NO: 17), GGATCTGCCCGCGGA (ASPH27; SEQ ID NO: 18), CGATCCTCTTGCGCAT (ASPH30; SEQ ID NO: 19), GGCGGGATGGCAT (ASPH35; SEQ ID NO: 20), GAC-CAGATGCAGGA (ASPH36; SEQ ID NO: 21), CTT-GCTCAGGATCTGCC (ASPH37; SEQ ID NO: 22), TCT-GTAGGAGGGC (ASPH45; SEQ ID NO: 23), CCTTAAGCCATCCATGA (ASPH48; SEQ ID NO: 24), TCTGAACTAGTACCGCC (ASPH65; SEQ ID NO: 25), TACTATTATGGCATCCC (ASPH69; SEQ ID NO: 26), AGCGTAATTGGTCATCA (ASPH71; SEQ ID NO: 27), GCGACCGTGACCAGAT (ASPH80; SEQ ID NO: 28), AACTAGTACCGCCTTT (ASPH82; SEQ ID NO: 29), GCGCGACCGTGACC (ASPH98; SEQ ID NO: 30), ACCACTAGAGCACC (ASPH105; SEQ ID NO: 31), AGCGCGACCGTGA (ASPH111; SEQ ID NO: 32), GGATCGCCTCGAT (ASPH112; SEQ ID NO: 33), CTAG-TACCGCCTT (ASPH115; SEQ ID NO: 34), CCGCG-GATCGCC (ASPH119; SEQ ID NO: 35), GACCGTGAC-CAGAT (ASPH121; SEQ ID NO: 36), and/or GACCGTGACCAGAT (ASPH153; SEQ ID NO: 37). In various embodiment, one or more nucleotide(s) of the oligonucleotide set forth herein (for example, in SEQ ID Nos.

1-37) is/are a LNA modified, wherein the modified nucleotide is a LNA, and/or an ENA, polyalkylene oxide-, 2'-fluoro-, 2'-0-methoxy-, and/or 2'0-methyl-modified nucleotide.

The term "cycle" as used herein refers to the number of days when the inhibitor of TGFβ is administered and number of days when the inhibitor of TGFβ is not administered. In an embodiment, one cycle is defined as administering the inhibitor for 7 days at a specific dosage per day and then not administering the inhibitor for 7 days. This is referred to as "7 days on and 7 days off" cycle. In another embodiment, one cycle is defined as administering the inhibitor for 4 days at a specific dosage per day and then not administering the inhibitor for 10 days. This is referred to as "4 days on and 10 days off cycle".

The term "PFS" as used herein refers to progression free survival and is a measure of the activity of a treatment on a disease. The term "OS" as used herein refers to overall survival and is a measure of the activity of the treatment and subsequent treatments, on a disease. As described herein, in some embodiments, if PFS is not improved upon administration of trabedersen or a variant, derivative or analog thereof but OS is improved upon administration of trabedersen or a variant, derivative or analog thereof, it is indicative of sensitization of the tumors by trabedersen or a variant, derivative or analog thereof to subsequent treatments.

The term "sensitization" as used herein refers to making the tumors sensitive to treatment. In one embodiment, trabedersen or a variant, derivative or analog thereof sensitizes tumors to subsequent exogenously administered therapies such as chemotherapy, radiation therapy, hormonal therapy or combination thereof. In another embodiment, trabedersen or a variant, derivative or analog thereof sensitizes tumors to the patient's own endogenous immune system. In exemplary embodiments, when a tumor is sensitized with trabedersen or a variant, derivative or analog thereof prior to chemotherapy, administration of one or more chemotherapeutic agents following treatment with trabedersen or a variant, derivative or analog thereof results in at least 10%, 20%, 30%, 40%, 50%, 60%, 70%, 80%, 90% or 100% improved response to the chemotherapeutic agents compared to treatment with the chemotherapeutic agents without sensitization with trabedersen or a variant, derivative or analog thereof.

"Trabedersen" or "trabedersen" as used herein refers to a transforming growth factor (TGF)-beta2 (TGFβ2) specific phosphorothioate antisense oligodeoxynucleotide with the sequence 5'-CGGCATGTCTATTTTGTA-3', as shown in SEQ ID No: 1. In exemplary embodiments, inhibitors of TGFβ, including inhibitors of TGFβ2 (such as trabedersen) are described in WO94/25588, WO95/17507, WO95/02051, WO98/33904, WO99/63975, WO01/68146, WO01/68122, WO03/064457, WO2005/014812, WO2004/093945, WO2005/059133, WO2005/084712, WO2006/11740, WO2008/077956A2, WO2010/055148, WO2011/012713A1, WO2011/154542, EP application no. 20100191103, WO2014154835 A2, WO2015/140150A1, the contents of each of which are herein incorporated by reference. In one embodiment, trabedersen is LNA modified. A LNA is a modified RNA nucleotide, wherein the ribose moiety is modified with an extra bridge connecting the 2' oxygen and 4' carbon (2'-4'ribonucleoside). The bridge "locks" the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and are mixable and combinable, respectively, with DNA or RNA residues in the oligonucleotide.

The inventor finds that administration of trabedersen to subjects with pancreatic cancer prior to administration of chemotherapeutic agents results in an increase in overall survival rates of the subjects. While not wishing to be bound by a single theory, the inventors hypothesize that administration of trabedersen or a variant, derivative or analog thereof prior to administration of chemotherapeutic agents sensitizes the pancreatic tumors to chemotherapeutic agents, radiation therapy, hormonal therapy and/or to the subject's own endogenous immune system. Accordingly, provided herein are compositions and methods for treating pancreatic cancer in a subject in need thereof, using trabedersen or a variant, derivative or analog thereof first, followed by other agents to treat pancreatic agents.

Compositions

Provided herein are compositions comprising a TGFβ signaling inhibitors and a pharmaceutically acceptable carrier. In various embodiments, a "TGFβ signaling inhibitor", "TGFβ signaling antagonist", "TGFβ signaling blocker", or "TGFβ signaling reducer" is any reagent that inhibits/blocks/reduces the TGFβ signaling, including inhibition/blockade/reduction of any molecular signaling step from the TGFβ ligand through its receptor to various downstream target molecules. As used herein, TGFβ includes but is not limited to TGFβ1, TGFβ2, or TGFβ3, or a combination thereof. In one embodiment, the TGFβ signaling inhibitor inhibits TGFβ1, TGFβ2 or TGFβ3. In another embodiment, the TGFβ signaling inhibitor inhibits TGFβ1 and TGFβ2 or TGFβ1 and TGFβ3 or TGFβ2 and TGFβ3. In a further embodiment, the TGFβ signaling inhibitor inhibits TGFβ1, TGFβ2 and TGFβ3.

In some embodiments, the TGFβ signaling inhibitor is a direct inhibitor of TGFβ or an indirect inhibitor of TGFβ. An indirect inhibitor of TGFβ may be an inhibitor of TGFβ receptor. In various embodiments, TGFβ signaling inhibitors include but are not limited to small molecules, antibodies or antigen-binding antibody fragments, intrabodies, aptamers, antisense oligonucleotides, RNA interference agents, and ribozymes.

Antibodies that specifically bind TGFβ (for example, TGFβ2) can be used for the inhibition of the TGFβ (for example, TGFβ2) in vivo. Alternatively, protein ligands for construction of TGFβ trap are also encompassed by the compositions and methods described herein. Antibodies to TGFβ (for example, TGFβ2) are commercially available and can be raised by one of skill in the art using well known methods. The TGFβ (for example, TGFβ2) inhibitory activity of a given antibody, or, for that matter, any TGFβ (for example, TGFβ2) inhibitor, can be assessed using methods known in the art or described herein. Antibody inhibitors of TGFβ (for example, TGFβ2) can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

In some embodiments, antibodies that may be used for TGFβ signaling inhibition for use in the methods described herein or in the compositions described herein include but are not limited to any one or more of Fresolimumad (GC-1008), Lerderlimumab (CAT-152), Metelimumab (CAT- 162), or combinations thereof. In further embodiments, TGFβ signaling inhibitors for use in the methods described herein or in the compositions described herein include but are not limited to any one or more of PF-03446962 antibody (a fully-human monoclonal antibody against transforming growth-factor β (TGFβ) receptor ALK1), Galunisertib (LY2157299, a small molecule inhibitor of TGFβ signaling), Lucanix (an allogenic tumor vaccine comprising a mixture of four allogeneic human non-small cell lung cancer cell lines modified to express an antisense oligonucleotide targeting TGFβ2) or TGFβ2 antisense oligonucleotide in combination with GM-CSF, or combinations thereof. It is contemplated that any of these TGFβ signaling inhibitors set forth herein may be used in the methods described herein to treat pancreatic cancer alone or in combination with chemotherapeutic agents and/or radiation therapy as set forth herein.

In an embodiment, the TGFβ signaling inhibitor is an antisense molecule that specifically targets a TGFβ. In some embodiments, the antisense molecule is an antisense nucleic acid, antisense polynucleotide, antisense polydeoxynucleotide, antisense oligonucleotide, or antisense oligodeoxynucleotide. The inhibition/blockade/reduction/decrease will be of at least 10%, 20%, 30%, 40%, 50%, 60%, 70%, 80%, 90%, 95% or 99% or more as compared to the expression of TGFβ gene or the activity or level of the TGFβ encoded by a TGFβ gene which has not been targeted by an antisense oligonucleotide. In certain embodiments, the TGFβ signaling inhibitor is a phosphorothioate antisense oligodeoxynucleotide specific for human TGFβ2 mRNA. In one embodiment, the TGFβ signaling inhibitor is trabedersen (AP12009) or a variant, derivative or analog thereof. In an embodiment, the TGFβ signaling inhibitor comprises, consists of or consists essentially of the sequence 5'-CGGCATGTCTATTTTGTA-3' as set forth in SEQ ID NO: 1. In some embodiments, there is no requirement for trabedersen or a variant, derivative or analog thereof to reduce the IC50 of chemotherapeutic agents and/or trabedersen or a variant, derivative or analog thereof does not reduce the $IC_{50}$ of chemotherapeutic agents. For example, as described herein in Examples 1 and 2, there was no advantage in combining trabedersen with temozolomide in glioma cells or in combining trabedersen in with 5-fluorouracil in pancreatic cancer cells or colon cancer cells.

Antisense oligodeoxynucleotide molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate (sulfur group) linkage, methyl phosphonate linkage (methyl group) or phosphoramidate (amine group) linkage. The antisense oligonucleotide strand can be derivatized with a reactive functional group of a reporter group, such as a fluorophore. Particularly useful derivatives are modified at a terminus or termini of an antisense oligonucleotide strand, typically the 3' terminus of the sense strand. For example, the 2'-hydroxyl at the 3' terminus can be readily and selectively derivatizes with a variety of groups. Other useful antisense oligonucleotide derivatives incorporate nucleotides having modified carbohydrate moieties, such as 2'-O-alkylated residues or 2'-O-methyl ribosyl derivatives or 2'-O-fluoro ribosyl derivatives or 2'-O-methylethyl ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition of TGFβ can also be incorporated. In some embodiments, antisense oligonucleotide modifications include 2'-deoxy-2'-fluorouridine or locked nucleic acid (LNA) nucleotides, peptide nucleic acid (PNA) nucleotides, morpholino phosphoroamidates (MF) nucleotides, or RNA duplexes containing either phosphodiester or varying numbers of phosphorothioate linkages. Such modifications are known to one skilled in the art and are described, for example, in Braasch et al., Biochemistry, 42: 7967-7975, 2003 or Mansoor and Melendez, Gene Regulation and Systems Biology, 2:275-295 2008.

In some embodiments as described herein, the TGFβ signaling inhibitor (such as trabedersen or a variant, derivative or analog thereof) inhibits TGFβ2 and may be used to treat subjects with disease-states that overexpress TGFβ2. In an embodiment, the disease-state is pancreatic cancer.

In further embodiments, the TGFβ2-specific antisense oligonucleotide (for example, trabedersen or a variant, derivative or analog thereof) is administered sequentially with a chemotherapeutic agent. In an embodiment, the TGFβ2-specific antisense oligonucleotide is administered prior to administration of the chemotherapeutic agent. In an embodiment, trabedersen or a variant, derivative or analog thereof is administered prior to administration of one or more chemotherapeutic agents and/or prior to administration of radiation therapy so as to sensitize the tumor to the chemotherapeutic agent and/or radiation therapy. In some embodiments, the TGFβ2-specific antisense oligonucleotide (such as trabedersen or a variant, derivative or analog thereof) sensitizes the tumor to the chemotherapeutic agent. In an embodiment, the TGFβ signaling inhibitor comprises, consists of or consists essentially of the sequence 5'-CGGCATGTCTATTTTGTA-3' as set forth in SEQ ID NO:1. In some embodiments, there is no requirement for trabedersen or a variant, derivative or analog thereof to reduce the IC50 of chemotherapeutic agents and/or trabedersen or a variant, derivative or analog thereof does not reduce the $IC_{50}$ of chemotherapeutic agents. For example, as described herein in Examples 1 and 2, there was no advantage in combining trabedersen with temozolomide in glioma cells or in combining trabedersen in with 5-fluorouracil in pancreatic cancer cells or colon cancer cells.

Typical dosages of an effective amount of the TGFβ signaling inhibitor (for example, TGFβ2 inhibitor) can be in the ranges recommended by the manufacturer where known molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In various embodiments, the TGFβ signaling inhibitor (such as trabedersen or a variant, derivative or analog thereof) is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg inhibitor/kg body weight, or a combination thereof. In various embodiments, the TGFβ signaling inhibitor (such as trabedersen or a variant, derivative or analog thereof) is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg inhibitor/m² body surface area, or a combination thereof. Here, "mg inhibitor/kg body weight" refers to mg inhibitor per kg body weight of the subject, and "mg inhibitor/m² body surface area" refers to mg inhibitor per m² body surface area of the subject.

In various embodiments, the effective amount of the TGFβ signaling inhibitor (such as trabedersen or a variant, derivative or analog thereof) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of the TGFβ signaling inhibitor (such as trabedersen or a variant, derivative or analog thereof) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/m²/day, or a combination thereof. In various embodiments, the effective amount of the TGFβ signaling inhibitor (such as trabedersen or a variant, derivative or analog thereof) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of the TGFβ signaling inhibitor (such as trabedersen or a variant, derivative or analog thereof) is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m²/day, or a combination thereof. Here, "µg/kg/day" or "mg/kg/day" refers to µg or mg inhibitor per kg body weight of the subject per day, and "µg/m²/day" or "mg/m²/day" refers to µg or mg inhibitor per m² body surface area of the subject per day.

In various embodiments, the TGFβ signaling inhibitor is trabedersen (AP12009) or a variant, derivative or analog thereof and is administered at about 50-100, 100-150, 150-200, 200-250, 250-300, 300-350, 350-400, 400-450, or 450-500 mg/m²/day. In some embodiments, trabedersen or a variant, derivative or analog thereof is administered at about 140, 150, 160, 170, or 180 mg/m²/day. In some embodiments, trabedersen or a variant, derivative or analog thereof is administered at about 310, 320, 330, 340, 350 mg/m²/day or a combination thereof.

In various embodiments, the TGFβ signaling inhibitor (such as trabedersen or a variant, derivative or analog thereof) may be administered once, twice, three or more times. In various embodiments, the TGFβ signaling inhibitor (such as trabedersen or a variant, derivative or analog thereof) may be administered 1-3 times per day, 1-7 times per week, 1-9 times per month, or 1-12 times per year. In various embodiments, the TGFβ signaling inhibitor (such as trabedersen or a variant, derivative or analog thereof) may be administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the TGFβ signaling inhibitor (such as trabedersen or a variant, derivative or analog thereof) may be administered once a day (SID/QD), twice a day (BID), three times a day (TID), four times a day (QID), or more, so as to deliver an effective amount of the TGFβ signaling inhibitor to the subject, where the effective amount is any one or more of the doses described herein.

In some embodiments, trabedersen or a variant, derivative or analog thereof is administered intravenously via continuous infusion for one, two, three, four, five or more cycles of 7 days and on 7 days off, prior to administration of a chemotherapeutic agent, radiation therapy or a combination thereof. In some embodiments, trabedersen or a variant, derivative or analog thereof is administered intravenously via continuous infusion for one, two, three, four, five or more cycles of 4 days on and 10 days off, prior to administration of a chemotherapeutic agent, radiation therapy or a combination thereof. In one embodiment, trabedersen or a variant, derivative or analog thereof is administered intravenously via continuous infusion for one cycle of 4 days on and 10 days off, prior to administration of a chemotherapeutic agent or radiation therapy. In one embodiment, trabedersen or a variant, derivative or analog thereof is administered intravenously via continuous infusion two cycles of 4 days on and 10 days off, prior to administration of a chemotherapeutic agent, radiation therapy or a combination thereof. In one embodiment, trabedersen or a variant, derivative or analog thereof is administered intravenously via continuous infusion three cycles of 4 days on and 10 days off, prior to administration of a chemotherapeutic agent, radiation therapy or a combination thereof. In one embodiment, trabedersen or a variant, derivative or analog thereof is administered intravenously via continuous infusion four cycles of 4 days on and 10 days off, prior to administration of a chemotherapeutic agent, radiation therapy or a combination thereof.

In accordance with the present invention, examples of the chemotherapeutic agent include but are not limited to Temozolomide, Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, liposome-encapsulated Doxorubicin such as Doxil (pegylated form), Myocet (nonpegylated form) and Caelyx, Epirubicin, Epothilone, Erlotinib, Etoposide, Fluorouracil, Folinic acid, Gefitinib, Gemcitabine, Hydroxyurea, Idarubicin, Imatinib, Ipilimumab, Irinotecan, Nanoliposomal Irinotecan (Nal-IRI), Mechlorethamine, Melphalan, Mercaptopurine, Methotrexate, Mitoxantrone, Ocrelizumab, Ofatumumab, Oxaliplatin, Paclitaxel, Taxol, Abraxane, Genexol, Protein-Bound Paclitaxel, Nab-Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

In various embodiments, the chemotherapeutic agent is a platinum-based antineoplastic agent. Examples of the platinum-based antineoplastic agent include but are not limited to oxaliplatin, cisplatin, lipoplatin (a liposomal version of cisplatin), carboplatin, satraplatin, picoplatin, nedaplatin, and triplatin, and their functional equivalents, analogs, derivatives, variants or salts.

In various embodiments, the chemotherapeutic agent is a taxane. Examples of the taxane include but are not limited to paclitaxel, docetaxel, and cabazitaxel, and their functional equivalents, analogs, derivatives, variants or salts, or formulations such as Abraxane, Taxol, Genexol.

In various embodiments, the chemotherapeutic agent is an anthracycline. Examples of the anthracycline include but are not limited to doxorubicin, daunorubicin, epirubicin, idarubicin, pirarubicin, aclarubicin, valrubicin, and mitoxantrone, and their functional equivalents, analogs, derivatives, variants or salts.

Typical dosages of an effective amount of the chemotherapeutic agent can be in the ranges recommended by the manufacturer where known molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In various embodiments, the chemotherapeutic agent is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg agent/kg body weight, or a combination thereof. In various embodiments, the chemotherapeutic agent is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg agent/$m^2$ body surface area, or a combination thereof. Here, "mg agent/kg body weight" refers to mg agent per kg body weight of the subject, and "mg agent/$m^2$ body surface area" refers to mg agent per $m^2$ body surface area of the subject.

In various embodiments, the effective amount of the chemotherapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of the chemotherapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/$m^2$/day, or a combination thereof. In various embodiments, the effective amount of the chemotherapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of the chemotherapeutic agent is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/$m^2$/day, or a combination thereof. Here, "µg/kg/day" or "mg/kg/day" refers to µg or mg agent per kg body weight of the subject per day, and "µg/$m^2$/day" or "mg/$m^2$/day" refers to µg or mg agent per $m^2$ body surface area of the subject per day.

In various embodiments, the chemotherapeutic agent may be administered once, twice, three or more times. In various embodiments, the chemotherapeutic agent may be administered 1-3 times per day, 1-7 times per week, 1-9 times per month, or 1-12 times per year. In various embodiments, the chemotherapeutic agent may be administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the chemotherapeutic agent may be administered once a day (SID/QD), twice a day (BID), three times a day (TID), four times a day (QID), or more, so as to deliver an effective amount of the chemotherapeutic agent to the subject, where the effective amount is any one or more of the doses described herein.

In accordance with the invention, the TGFβ signaling inhibitor and/or the chemotherapeutic agent may be administered using the appropriate modes of administration, for instance, the modes of administration recommended by the manufacturer where known molecules or compounds are used. As described herein, the TGFβ signaling inhibitor (for example, trabedersen or a variant, derivative or analog thereof) and chemotherapeutic agent are administered sequentially, wherein the TGFβ signaling inhibitor (for example, trabedersen or a variant, derivative or analog thereof) is administered prior to administration of chemotherapy or radiation therapy. In accordance with the invention, various routes may be utilized to administer the TGFβ signaling inhibitor and the chemotherapeutic agent of the claimed composition and methods, including but not limited to intratumoral, intravascular, intravenous, intraarterial, intramuscular, subcutaneous, intraperitoneal, aerosol, nasal, via inhalation, oral, transmucosal, transdermal, parenteral, implantable pump or reservoir, continuous infusion, enteral application, topical application, local application, capsules and/or injections. In various embodiments, the TGFβ signaling inhibitor can be administered intracranially, intraventricularly, intrathecally, epidurally, intradurally, topically, intratumorally, intravascularly, intravenously, intraarterially, intramuscularly, subcutaneously, intraperitoneally, intranasally, or orally. In various embodiments, the chemotherapeutic agent can be administered intracranially, intraventricularly, intrathecally, epidurally, intradurally, topically, intratumorally, intravascularly, intravenously, intraarterially, intramuscularly, subcutaneously, intraperitoneally, intranasally, or orally. In some embodiments, the TGFβ signaling inhibitor (for example, trabedersen or a variant, derivative or analog thereof) and the chemotherapeutic agent are administered using the same route. In some embodiments, the TGFβ signaling inhibitor and the chemotherapeutic agent are administered using different routes.

In various embodiments, the compositions according to the invention can contain any pharmaceutically acceptable excipient. As used herein, an "excipient" is a natural or synthetic substance formulated alongside the active ingredient of a composition or formula, included for the purpose of bulking-up the composition or formula. Thus, "excipient" is often referred to as "bulking agent", "filler", or "diluent". For a non-limiting example, one or more excipients may be added to a composition described herein and increase the composition's volume or size so that one serving of the composition fits into one capsule or tablet. Also, an "excipient" may confer an enhancement on the active ingredients in the final dosage form, such as facilitating absorption or solubility of the active ingredients. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The compositions according to the invention can also be in liposomes, encapsulated, tableted or prepared in an emulsion or syrup for oral administration. In some embodiments, liposomes comprising trabedersen or a variant, derivative or analog thereof are coated with tissue specific antibodies. In certain embodiments, the composition comprising trabedersen or a variant, derivative or analog thereof is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The compositions are made following the conventional techniques of pharmacy involving dry milling, mixing, and blending for powder forms; milling, mixing, granulation, and compressing, when necessary, for tablet forms; or milling, mixing and filling for hard gelatin capsule forms.

When a liquid carrier is used, the preparation will be in the form of a syrup, elixir, emulsion or an aqueous or non-aqueous suspension. Such a liquid formulation may be administered directly p.o. or filled into a soft gelatin capsule.

The compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980)

9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In various embodiments, the subject is a human. In various embodiments, the subject is a mammalian subject including but not limited to human, monkey, ape, dog, cat, cow, horse, goat, pig, rabbit, mouse and rat. In some embodiments, the subject is an animal model of a cancer.

Methods

Provided herein are methods for sensitizing a tumor to antitumor therapies in a subject in need thereof. The methods comprise, consist of or consist essentially of providing a composition comprising an inhibitor of TGFβ signaling and administering an effective amount of the composition to the subject so as to sensitize the tumor. In one embodiment, the tumor is a pancreatic tumor. In another embodiment, the inhibitor of TGFβ signaling is an antisense oligonucleotide specific for TGFβ2. In an embodiment, the antisense oligonucleotide specific for TGFβ2 is trabedersen or a variant, derivative or analog thereof.

In some embodiments, methods for treating, inhibiting, reducing the severity of or preventing metastasis of cancer in a subject in need thereof include first sensitizing the tumor using the TGFβ signaling inhibitor as set forth herein and subsequently administering exogenous therapeutic agents including chemotherapeutic agents, radiation therapy or a combination thereof.

Also provided herein are methods for treating cancer in a subject in need thereof. The methods comprise, consist of or consist essentially of providing a composition comprising an inhibitor of TGFβ signaling and administering an effective amount of the composition to the subject so as to treat cancer in the subject. In one embodiment, the cancer is pancreatic cancer. In another embodiment, the inhibitor of TGFβ signaling is an antisense oligonucleotide specific for TGFβ2. In an embodiment, the antisense oligonucleotide specific for TGFβ2 is trabedersen or a variant, derivative or analog thereof. The methods further comprise administering exogenous therapies including chemotherapy, radiation therapy, hormonal therapy or a combination thereof. In some embodiments, trabedersen or a variant, derivative or analog thereof is administered prior to administration of chemotherapeutic agents, radiation therapy or a combination thereof as described herein.

Further provided herein are methods for inhibiting cancer in a subject in need thereof. The methods comprise, consist of or consist essentially of providing a composition comprising an inhibitor of TGFβ signaling and administering an effective amount of the composition to the subject so as to inhibit cancer in the subject. In one embodiment, the cancer is pancreatic cancer. In another embodiment, the inhibitor of TGFβ signaling is an antisense oligonucleotide specific for TGFβ2. In an embodiment, the antisense oligonucleotide specific for TGFβ2 is trabedersen or a variant, derivative or analog thereof. The methods further comprise administering exogenous therapies including chemotherapy, radiation therapy, hormonal therapy or a combination thereof. In some embodiments, trabedersen or a variant, derivative or analog thereof is administered prior to administration of chemotherapeutic agents, radiation therapy or a combination thereof as described herein Also provided herein are methods for reducing the severity of cancer in a subject in need thereof. The methods comprise, consist of or consist essentially of providing a composition comprising an inhibitor of TGFβ signaling and administering an effective amount of the composition to the subject so as to reduce the severity of cancer in the subject. In one embodiment, the cancer is pancreatic cancer. In another embodiment, the inhibitor of TGFβ signaling is an antisense oligonucleotide specific for TGFβ2. In an embodiment, the antisense oligonucleotide specific for TGFβ2 is trabedersen or a variant, derivative or analog thereof. The methods further comprise administering exogenous therapies including chemotherapy, radiation therapy, hormonal therapy or a combination thereof. In some embodiments, trabedersen or a variant, derivative or analog thereof is administered prior to administration of chemotherapeutic agents, radiation therapy or a combination thereof as described herein.

Additionally provided herein are methods for preventing metastasis of cancer in a subject in need thereof. The methods comprise, consist of or consist essentially of providing a composition comprising an inhibitor of TGFβ signaling and administering an effective amount of the composition to the subject so as to prevent metastasis of cancer in the subject. In one embodiment, the cancer is pancreatic cancer. In another embodiment, the inhibitor of TGFβ signaling is an antisense oligonucleotide specific for TGFβ2. In an embodiment, the antisense oligonucleotide specific for TGFβ2 is trabedersen or a variant, derivative or analog thereof. The methods further comprise administering exogenous therapies including chemotherapy, radiation therapy, hormonal therapy or a combination thereof. In some embodiments, trabedersen or a variant, derivative or analog thereof is administered prior to administration of chemotherapeutic agents, radiation therapy or a combination thereof as described herein.

Further provided herein are methods for reducing the tumor load of a pancreatic tumor in a subject in need thereof. The methods comprise, consist of or consist essentially of providing a composition comprising an inhibitor of TGFβ signaling and administering an effective amount of the composition to the subject so as to reduce the pancreatic tumor load in the subject. In one embodiment, the inhibitor of TGFβ signaling is an antisense oligonucleotide specific for TGFβ2. In an embodiment, the antisense oligonucleotide specific for TGFβ2 is trabedersen or a variant, derivative or analog thereof. The methods further comprise administering exogenous therapies including chemotherapy, radiation therapy, hormonal therapy or a combination thereof. In some embodiments, trabedersen or a variant, derivative or analog thereof is administered prior to administration of chemotherapeutic agents, radiation therapy or a combination thereof, as described herein.

In some embodiments of the methods described herein, the TGFβ signaling inhibitor is an antisense molecule that specifically targets a TGFβ. In some embodiments, the antisense molecule is an antisense nucleic acid, antisense polynucleotide, antisense polydeoxynucleotide, antisense oligonucleotide, or antisense oligodeoxynucleotide. The inhibition/blockade/reduction/decrease will be of at least 10%, 20%, 30%, 40%, 50%, 60%, 70%, 80%, 90%, 95% or 99% or more as compared to the expression of TGFβ gene or the activity or level of the TGFβ encoded by a TGFβ gene which has not been targeted by an antisense oligonucleotide. In certain embodiments, the TGFβ signaling inhibitor is a phosphorothioate antisense oligodeoxynucleotide specific for human TGFβ2 mRNA. In one embodiment, the TGFβ signaling inhibitor is trabedersen (AP12009), or a variant, derivative or analog thereof. In an embodiment, the TGFβ signaling inhibitor comprises, consists of or consists essentially of the sequence 5'-CGGCATGTCTATTTTGTA-3' as set forth in SEQ ID NO: 1. In some embodiments, there is no requirement for trabedersen or a variant, derivative or analog thereof to reduce the IC50 of chemotherapeutic agents and/or trabedersen or a variant, derivative or analog thereof does not reduce the $IC_{50}$ of chemotherapeutic agents. For example, as described herein in Examples 1 and 2, there was no advantage in combining trabedersen with temozolomide in glioma cells or in combining trabedersen in with 5-fluorouracil in pancreatic cancer cells or colon cancer cells.

In some embodiments of the methods described herein, trabedersen or a variant, derivative or analog thereof is administered intravenously via continuous infusion for one, two, three, four, five or more cycles of 7 days and on 7 days off, prior to administration of a chemotherapeutic agent or radiation therapy. In some embodiments, trabedersen or a variant, derivative or analog thereof is administered intravenously via continuous infusion for one, two, three, four, five or more cycles of 4 days on and 10 days off, prior to administration of a chemotherapeutic agent or radiation therapy. In one embodiment, trabedersen or a variant, derivative or analog thereof is administered intravenously via continuous infusion for one cycle of 4 days on and 10 days off, prior to administration of a chemotherapeutic agent or radiation therapy. In one embodiment, trabedersen or a variant, derivative or analog thereof is administered intravenously via continuous infusion two cycles of 4 days on and 10 days off, prior to administration of a chemotherapeutic agent or radiation therapy. In one embodiment, trabedersen or a variant, derivative or analog thereof is administered intravenously via continuous infusion three cycles of 4 days on and 10 days off, prior to administration of a chemotherapeutic agent or radiation therapy. In one embodiment, trabedersen or a variant, derivative or analog thereof is administered intravenously via continuous infusion four cycles of 4 days on and 10 days off, prior to administration of a chemotherapeutic agent or radiation therapy.

In various embodiments of the methods described herein, the chemotherapeutic agent for use with the methods described herein include but are not limited to Temozolomide, Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Dacarbazine, Daunorubicin, Docetaxel, Doxifluridine, Doxorubicin, liposome-encapsulated Doxorubicin such as Doxil (pegylated form), Myocet (nonpegylated form) and Caelyx, Epirubicin, Epothilone, Erlotinib, Etoposide, Fluorouracil, Folinic acid, Gefitinib, Gemcitabine, Hydroxyurea, Idarubicin, Imatinib, Ipilimumab, Irinotecan, Nanoliposomal Irinotecan (Nal-IRI), Mechlorethamine, Melphalan, Mercaptopurine, Methotrexate, Mitoxantrone, Ocrelizumab, Ofatumumab, Oxaliplatin, Paclitaxel, Taxol, Abraxane, Genexol, Protein-Bound Paclitaxel, Nab-Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, prednisone, methylprednisolone, dexamethasone or a combination thereof.

In various embodiments of the methods described herein, exogenous therapies for use with the methods described herein include radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or tele-therapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments of the methods described herein, exogenous therapies for use with the methods described herein include hormonal therapy. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

As described herein, typical dosages of an effective amount of the TGFβ inhibitor (for example, TGFβ2 inhibitor) can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the compositions of the invention comprising the TGFβ inhibitor (for example, TGFβ2 inhibitor) may be administered once a day (SID/QD), twice a day (BID), three times a day (TID), four times a day (QID), or more, so as to administer an effective amount of the TGFβ inhibitor (for example, TGFβ2 inhibitor) to the subject, where the effective amount is any one or more of the doses described herein.

In various embodiments, the subject is selected from the group consisting of human, non-human primate, monkey, ape, dog, cat, cow, horse, rabbit, mouse and rat.

Typical dosages of an effective amount of the TGFβ signaling inhibitor (for example, TGFβ2 inhibitor or a composition comprising TGFβ2 inhibitor) for use with methods of the invention are described herein. These dosages can be in the ranges recommended by the manufacturer where known molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In various embodiments, the TGFβ signaling inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg inhibitor/kg body weight, or a combination thereof. In various embodiments, the TGFβ signaling inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg inhibitor/m$^2$ body surface area, or a combination thereof. Here, "mg inhibitor/kg body weight" refers to mg inhibitor per kg body weight of the subject, and "mg inhibitor/m$^2$ body surface area" refers to mg inhibitor per m$^2$ body surface area of the subject.

In various embodiments, the effective amount of the TGFβ signaling inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of the TGFβ signaling inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/m$^2$/day, or a combination thereof. In various embodiments, the effective amount of the TGFβ signaling inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of the TGFβ signaling inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/m$^2$/day, or a combination thereof. Here, "µg/kg/day" or "mg/kg/day" refers to µg or mg inhibitor per kg body weight of the subject per day, and "µg/m$^2$/day" or "mg/m$^2$/day" refers to µg or mg inhibitor per m$^2$ body surface area of the subject per day.

In various embodiments, the TGFβ signaling inhibitor is trabedersen (AP12009) or a variant, derivative or analog thereof, and it is administered at about 50-100, 100-150, 150-200, 200-250, 250-300, 300-350, 350-400, 400-450, or 450-500 mg/m$^2$/day. In some embodiments, trabedersen or a variant, derivative or analog thereof is administered at about 140, 150, 160, 170, or 180 mg/m$^2$/day. In some embodiments, trabedersen or a variant, derivative or analog thereof is administered at about 310, 320, 330, 340, or 350 mg/m$^2$/day.

In various embodiments, the TGFβ signaling inhibitor may be administered once, twice, three or more times. In various embodiments, the TGFβ signaling inhibitor may be administered 1-3 times per day, 1-7 times per week, 1-9 times per month, or 1-12 times per year. In various embodiments, the TGFβ signaling inhibitor may be administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the TGFβ signaling inhibitor may be administered once a day (SID/QD), twice a day (BID), three times a day (TID), four times a day (QID), or more, so as to deliver an effective amount of the TGFβ signaling inhibitor to the subject, where the effective amount is any one or more of the doses described herein.

Advantages of the Invention

TGFβ2 is overexpressed in many advanced tumors where it generates a microenvironment that cloaks the tumor and promotes immune evasion in patients. This makes it challenging for therapeutic agents such as chemotherapies to reach the tumor cells. Herein, the inventor shows for the first time that inhibition of TGFβ2 using trabedersen un-cloaks the tumor, thus sensitizing it to subsequent chemotherapies, showing the importance of the order in which the therapeutic agents are administered. U.S. Pat. No. 8,476,246 shows that when cells lines are co-treated with trabedersen and chemotherapeutic agents (such as gemcitabine or temozolomide), the $IC_{50}$ of the chemotherapeutic agents is reduced; however, the effect of co-administration trabedersen and chemotherapeutic agents on the tumor load or overall survival is unclear. In contrast, the inventor shows that when patients are administered trabedersen and a chemotherapeutic agent sequentially and trabedersen is administered prior to the chemotherapeutic agent, there is a significant increase in the overall survival rate of patients. Further, the inventor also shows that if chemotherapy precedes treatment with trabedersen or if treatment with trabedersen is not followed by chemotherapy, then the overall patient survival rate is significantly reduced. Thus the instant invention provides an unexpected advantage, namely, that treatment of pancreatic cancer patients with trabedersen (for an effective number of cycles as described herein) prior to treatment with a chemotherapeutic agent significantly increases the overall survival rate in patients with pancreatic cancer patients.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

The aim of the study was to determine the effect of AP12009 (trabedersen) treatment in combination with 5-Fluorouracil (5-FU) on TGFβ2 secretion and on cellular proliferation of HUP-T3 pancreatic cancer cells and WiDr colon cancer cells in vitro.

In HUP-T3 pancreatic cancer cells 5-FU (treatment on day 1 for 5 h) at concentrations>10 μM dose-dependently reduced cell proliferation measured after 7 days. TGFβ2 was only suppressed at concentrations higher than ca. 75 μM 5-FU. 10 μM of AP12009 as monotherapy decreased cell proliferation (53% proliferation of untreated control) and TGFβ2 expression (42% of untreated control) in HUP-T3 cells. Adding 10 μM of AP12009 to 5-FU did not result in any additional inhibition of proliferation compared with 5-FU alone. Addition of 5-FU to 10 μM AP12009 resulted in sub-additive or even antagonistic effects regarding inhibition of TGFβ2 expression.

In WiDr colorectal cancer cells 5-FU (treatment on day 1 for 5 h only) concentration-dependently reduced cell proliferation at concentrations higher than ca. 38 μM. TGFβ2 was only suppressed at concentrations higher than ca. 75 μM 5-FU. 10 μM of AP12009 slightly decreased cell proliferation (76% of untreated control) and had a more pronounced effect on TGFβ2 expression (54% of untreated control). Combination of 10 μM AP12009 and 5-FU resulted in sub-additive effects on cell proliferation and TGFβ2 expression.

In summary, no beneficial results were observed by combination of AP12009 with 5-FU in HUP-T3 and WiDr cells.

Example 2

A-172 glioma cells were treated with a combination of AP12009 (trabedersen) 0 to 10 μM and different concentrations of TMZ (temozolomide) for 7 days (treatment schedule 2*2/1*3 d).

A pre-treatment (1*2/1*3d) of A-172 glioma cells with AP12009, before combined treatment with AP12009 and TMZ (2*2/1*3d) did not show any benefit. A single treatment (day 0) with TMZ for one day combined with a 7 day AP12009 treatment (2*1/1*2/1*3d) did not show any benefit or disadvantage. High TMZ concentrations (64/160/400 μM) dose-dependently reduced migration of A-172 cells as monotherapy. AP12009 (10 μM) as monotherapy did not affect migration compared with untreated control. In combination, AP12009 did not influence the effects of TMZ on migration.

TMZ dose dependently reduced proliferation and TGF-β2 in parallel. AP12009 strongly reduced TGFβ2 and slightly reduced cell proliferation. In combination, an additive effect on inhibition of TGFβ2 secretion was observed, while no reproducible beneficial effect on cell proliferation could be detected. Lactase dehydrogensa (LDH) release assay for quantification of cytotoxity did not show reproducible results. In summary there is no clear beneficial effect in combining AP12009 with TMZ in A-172 cells.

Example 3

Phase 1/2 Trial of Treatment with Trabedersen

Over-expression of transforming growth factor-beta 2 (TGF-β2) is associated with poor prognosis and plays a key role for malignant progression of various tumors by inducing proliferation, metastasis, angiogenesis and immunosuppression. P-001 trial of trabedersen—Safety and Tolerability of AP 12009 (trabedersen), Administered I.V. in Patients With Advanced Tumors Known to Overproduce TGFβ2, was evaluated to determine if treatment with trabedersen primed the tumors to subsequent chemotherapy.

In the instant study, the primary objective was to determine the Maximum Tolerated Dose (MTD) and the Dose Limited Toxicity (DLT) of two cycles of trabedersen administered intravenously (i.v.) for either 7 days every other week (i.e. 7 days on/7 days off) or for 4 days every other week (4 days on/10 days off). The secondary objective included assessment of antitumor activity of trabedersen administered intravenously for either 7 days every other week (i.e. 7 days on/7 days off) or for 4 days every other week (4 days on/10 days off).

Open-Label Phase I/II Dose Escalation Study

The escalation scheme of this study aimed to determinate the MTD of two cycles of trabedersen (so called 'core study period') administered as a continuous i.v. infusion for 7 days every other week (7-days-on/7-days-off) or for 4 days every other week (4-days-on/10-days-off).

In general, it was planned to enroll a cohort of at least 3 evaluable patients per treatment group. For each cohort, the safety data obtained until end of the core study period (period for DLT-assessment, Cycle 1 and Cycle 2) were assessed in an interim analysis and evaluated by a Data and Safety Monitoring Board (DSMB). If the results indicated that the treated patients had tolerated this regimen, then the next cohort of 3 evaluable patients received the next higher dose. If 2 of these 3 patients experienced a DLT, the number of evaluable patients for the subsequent treatment group was increased to 6 for further evaluation of toxicity. Patients who were withdrawn from the study due to adverse events (AEs) attributed to DLT by the treating clinician, were not replaced but were used to determine the MTD and to evaluate the safety of the study drug. If patients were withdrawn due to other reasons, they were replaced until the treatment group was complete.

The MTD was determined according to the following procedure: If 2 out of 3 patients of 1 cohort experienced a DLT, 3 more patients were enrolled in the same treatment group. If at least 1 of these additional 3 patients also met the toxicity criteria for a DLT, the MTD for two cycles was determined; otherwise the dose escalation was continued upon agreement with the DSMB. MTD for two cycles was then defined as the dose at which no more than 2 out of 3, or 2 out of 6 patients of the same treatment group experienced a DLT. This procedure was followed until the MTD was reached.

After dose escalation had been completed, an additional larger cohort of patients was enrolled and treated with a dose of 140 mg/m$^2$/day employing the 4-days-on/10-days-off schedule, with endorsement by the DSMB. This cohort was to include at least 12 patients with a histologically or cytologically confirmed diagnosis of stage III or IV pancreatic cancer, corresponding to AJCC 1997 stage IVa and IVb, respectively, and at least 12 patients with stage III or IV melanoma.

The end of the study was defined as the point at which one of the following criteria had been met for all patients of the last cohort: (1) a time-point of twelve months after enrollment of the last patient had been reached, or (2) Median overall survival (OS) was reached for the last cohort (i.e. more than half of the patients had died during follow-up).

Despite an expected low toxicity profile for the lower dose groups based on the preclinical toxicology results, no accelerated escalation was done and 3 evaluable patients per dose group were included from the start. Accelerated escalation was not done because such patients typically show a complex range of disease-related symptoms that may have overlapped with potential toxicities of trabedersen; consequently, 3 evaluable patients provided more information allowing a better assessment of drug-related toxicities. In general, patients were enrolled in a chronological order, but at least 1 patient per disease population should ideally have been included in each treatment group if possible, in particular in the higher dose groups where first toxicities were observed.

Study Patients

A total of 62 patients were enrolled in the study; 38 patients with pancreatic cancer, 19 patients with melanoma, and 5 patients with colorectal cancer. All patients, except 1 pancreatic cancer patient, were treated with trabedersen and thus the safety population/full analysis set (FAS) comprised 61 patients. Seven patients with pancreatic cancer, 1 patient with melanoma, and 3 patients with colorectal cancer dropped out during the core study; consequently, 50 patients completed the core study (30 with pancreatic cancer, 18 with melanoma, and 2 with colorectal cancer).

After the core study period, 25 pancreatic cancer patients, 16 melanoma patients, and 1 colorectal patient continued treatment in the extension study period during which most of these patients discontinued prematurely before receiving a total of 10 treatment cycles. 3 patients with pancreatic cancer and 1 with melanoma completed the full extension study period. Of note, investigators were asked to discontinue the treatment of patients after the 4th treatment cycle if signs of progressive disease were observed at that time point.

Of the 61 patients enrolled, 52 patients (30 with pancreatic cancer, 18 with melanoma and 4 with colorectal cancer) were presented to the DSMB for DLT assessment in the core study period (Cycle 1 and Cycle 2) as they fulfilled the respective criteria as defined in the protocol. The mean age was 60.3 years (+9.6 years). All patients were Caucasian. Seventeen patients (45.9%) presented with pancreatic cancer, 8 patients (42.1%) with melanoma, and 5 patients (100%) with colorectal cancer were male. The mean weight at baseline was lower in pancreatic cancer patients (65.4 kg) than in melanoma (78.3 kg) or colorectal cancer patients (78.6 kg).

Inclusion Criteria

The inclusion criteria for this study were as follows: (1) The patient provided written informed consent prior to any study-related procedure; (2) The patient was at least 18 years of age and not older than 75 years; (3) The patient was a male or a non-pregnant, non-lactating female. (4) Patients with pancreatic cancer had a histologically or cytologically confirmed diagnosis of pancreatic cancer, stage III or IV (AJCC 2002, corresponds to AJCC 1997 stage IVA or IVB); (5) Patients with melanoma had a histologically or cytologically confirmed diagnosis of melanoma, stage III or IV (AJCC 2002); (6) Patients with colorectal cancer had a histologically or cytologically confirmed diagnosis of colorectal cancer, stage III or IV (AJCC 2002) (excluded from the last cohort); (7) The patient was not or no longer amenable to established forms of therapy; (8) The patient had at least 1 measurable lesion; (9) The patient had a Karnofsky performance status of at least 80%; (10) The patient had recovered from acute toxicity caused by any previous therapy; and (11) The patient showed adequate organ function as assessed by the following laboratory values: (a) Serum creatinine and urea<2 times the upper limit of normal (ULN); (b) Alanine aminotransferase (ALT) and aspartate aminotransferase (AST)<3 ULN (in case of a liver metastasis: <5×ULN); Alkaline phosphatase (AP)<3 ULN; and bilirubin<2.5 mg/dL; (c) Prothrombin time (PT)<1.5 international normalized ratio (INR) and partial thromboplastin time (PTT)<1.5 times the ULN; (d) Hemoglobin>9 g/dL; (e) Platelets>100×109/L; (f) White blood cell (WBC) count>3.0×109/L; and (g) Absolute Neutrophil Count (ANC)>1.5×109/L.

Exclusion Criteria

The exclusion criteria for this study were as follows: (1) The patient was unable to comply with the protocol regulations; (2) The patient was a pregnant or lactating female; (3) The patient had received antitumor radiation therapy within 12 weeks, tumor surgery within 4 weeks or any other therapy with established antitumor effects within 2 weeks prior to study entry; (4) The patient was taking or was likely to need other prohibited concomitant medication; administration of corticosteroids was strictly avoided during the course of the study; (5) The patient had participated in another clinical trial with investigational medication within 30 days prior to study entry; (6) The patient had a history of brain metastases. If brain metastases were suspected, a computed tomography (CT) scan of the skull was performed. This was not mandatory in asymptomatic patients; (7) The patient showed clinically significant cardiovascular abnormalities such as refractory hypertension, congestive heart failure, unstable angina pectoris, or poorly controlled arrhythmia, or had a myocardial infarction within 6 months prior to treatment; (8) The patient had gastric or duodenal ulcers within 6 months before study entry or was at risk of gastrointestinal ulceration due to high consumption of non-steroidal anti-inflammatory (NSAIDs); (9) The patient had an active infection with human immunodeficiency virus (HIV), hepatitis B virus (HBV), or hepatitis C virus (HCV); (10) The patient had a clinically significant acute viral, bacterial, or fungal infection; (11) The patient had acute medical problems that may have been considered to become an unacceptable risk, or any conditions that might have been contraindications for starting study treatment; (12) The patient had a history of allergies to reagents used in this study; (13) The patient was known for drug abuse or extensive use of alcohol; (14) The patient showed significant psychiatric disorders/legal incapacity or limited legal capacity; (15) The patient had a history of Long QT Syndrome or an average heart rate-corrected QT interval (QTc) time≥480 msec. The average QTc time was calculated from 3 separate electrocardiograms (ECGs) performed prior to the start of infusion: 2 ECGs at screening/baseline (with 1 hour minimum interval in between) and 1 ECG within 1 hour prior to start of infusion.

The clinical starting dose for the 7-days-on and 7-days-off schedule was based on the Lowest-Observed-Adverse-Effect-Level (LOAEL) devoid of severe toxicity in Cynomolgus monkeys as the most relevant species. This LOAEL of 4 mg/kg body weight (b.w.)/day is equivalent to approximately 1.3 mg/kg b.w./day or 48 mg/m$^2$/day on a body surface area basis in human adults. These numbers were rounded down and the safe starting dose was defined at 40 mg/m$^2$/day, equivalent to approximately 1 mg/kg b.w./day in humans. An alternative approach would have been based on the lowest lethal dose (LLD) of 300 mg/kg b.w. obtained in the acute single dose toxicity study in mice (in rats it was determined at 1000 mg/kg), at which 1 of 10 mice died (LLD10). According to the standard method, 10% of this dose (30 mg/kg) on a body surface area basis would then be defined as the clinical starting dose resulting in 90 mg/m$^2$/day. In the end, the lower of the two alternatives was chosen as starting dose.

For determination of the starting dose for 4-days-on and 10-days-off schedule, the cumulative dose of study medication per treatment cycle (instead of the daily dose) had been taken into consideration. The daily dose of the proposed 4-days-on and 10-days-off schedule (140 mg/m$^2$/day or 560 mg/m$^2$/cycle or approx. 3.5 mg/kg/day) still remained slightly below the daily dose of MTD of the initial 7-days-on and 7-days-off schedule (approx. 4 mg/kg/day). In addition the dose was administered only for 4 instead of 7 days. Therefore, the starting dose of 140 mg/m$^2$/day for the 4-days-on, 10-days-off schedule was assessed as safe by the DSMB as well as by the Coordinating Investigator. Based upon the adverse events observed for the various doses of the 7-days-on and 7-days-off schedule, it was decided to explore doses of up to 330 mg/m$^2$/day for the 4-days-on and 10-days-off schedule.

In spite of non-lipophilic properties of trabedersen, an adjustment to the body surface area was done to accommodate the usual practice in oncology and the participating study centers.

Safety Evaluation

The safety population comprised of 61 patients, representing all patients for whom at least once a trabedersen infusion was started. According to the protocol, the MTD was determined according to the following procedure: if 2 out of 3 patients of one cohort experience dose-limiting toxicity, 3 more patients were enrolled in the same treatment group. If at least 1 more patient of this second cohort met the toxicity criteria, MTD for two cycles has been determined (otherwise escalation was continued). MTD for two cycles was then defined as the dose at which no more than 2 out of 3 or 2 out of 6 patients of the same treatment group experienced DLT. Consistently, if 3 patients of the first cohort showed DLT, the second cohort was left out. In the case that 2 patients of the first cohort experienced DLTs that clearly indicated attainment of the MTD, the second cohort could also be omitted. The described procedure was pursued until the MTD is reached.

The number of patients per cohort of the 7-days-on and 7-days-off and 4-days-on and 10-days-off dose escalation schedules varied between 3 and 6 patients. The last cohort treated with 140 mg/m$^2$/day with the 4-days-on and 10-days-off schedule contained 28 patients (14 each with pancreatic cancer and melanoma). The median number of cycles per cohort varied between 1.5 and 5.0. The median trabedersen dose per day during the core study period reflected the respective dose cohort, with the highest median dose per day seen for cohort 4 of the 7-days-on and 7-days-off schedule (167.9 mg/m$^2$/day).

MTD for 7 days on and 7 days off regimen (N=1) was 160 mg/m$^2$/d whereas MTD was not reached on 4 days on and days off regimen (N=27) even at highest dose of 330 mg/m$^2$/d.

For a total of 4 patients, 2 patients with pancreatic carcinoma and 2 patients with colorectal cancer, a DLT was proclaimed. Since 3 of these patients experienced the DLT (2 cases of Grade 3 thrombocytopenia, 1 case of Grade 3 maculopapular rash) while receiving 240 mg/m$^2$/day in the 7-days-on and 7-days-off schedule, the next lower dosing regimen of 160 mg/m$^2$/day was identified as the MTD for the 7-days-on and 7-days-off schedule.

The fourth patient experienced a dose-limiting Grade 3 upper gastrointestinal hemorrhage after he had been infused with 140 mg/m$^2$/day in the 4-days-on and 10-days-off schedule. No other DLTs were observed in the 4-days-on and 10-days-off schedule and therefore no MTD was established for that schedule (highest dose test 330 mg/m$^2$/day).

During the study, 14 patients (23.0%) experienced a total of 23 treatment emergent adverse events (TEAEs) that led to treatment discontinuation: 9 patients (24.3%) with pancreatic cancer, 3 (15.8%) with melanoma, and 2 (40.0%) with colorectal cancer. The frequency of patients that experienced a TEAE leading to treatment discontinuation was substantially higher with the 7-days-on and 7-days-off schedule (7 patients [41.2%]) than for patients treated with the 4-days-on and 10-days-off schedule (7 [15.9%]). And as shown in Table 1, the serious adverse events (SAEs) was higher for the 7-days-on, 7-days off schedule than the 4-days-on, 10-days off schedule.

TABLE 1

Serious Adverse Events (SAE) reported by ≥2 Patients, by Schedule and Sorted by Frequency. No. (%) of patients with SAE/No. of SAEs

| Preferred Term | 7-days-on, 7-daysoff schedule/(N = 17) | 4-days-on, 10-daysoff schedule/(N = 44) | Total/ (N = 61) |
|---|---|---|---|
| Any SAE | 12 (70.6)/28 | 18 (40.9)/28 | 30 (49.2)/56 |
| Cholangitis | 1(5.9)/1 | 3 (6.8)/3 | 4 (6.6)/4 |
| Ascites | 3 (17.6)/3 | 0 | 3 (4.9)/3 |
| Catheter related Infection | 2 (11.8)/2 | 1(2.3)/1 | 3 (4.9)/3 |
| GI hemorrhage | 2 (11.8)/3 | 1 (2.3)/2 | 3 (4.9)/3 |
| Pneumonia | 3 (17.6)/3 | 0 | 3 (4.9)/3 |
| Cancer Pain | 0 | 2 (4.5)/2 | 2 (3.3)/2 |
| Cholestasis | 1 (5.9)/1 | 1 (2.3)/1 | 2 (3.3)/2 |
| Upper GI hemorrhage | 1 (5.9)/1 | 1(2.3)/1 | 2 (3.3)/2 |

N = total number of patients;
No. = number;
SAE = serious adverse event.

Efficacy Evaluation

At screening, up to 10 "measurable lesions" (i.e. lesions that could be accurately measured in at least 1 dimension with a longest diameter of 2 cm) representative of all involved organs were identified as "target lesions" for tumor response assessment and were measured and documented. All other lesions were defined and recorded as "non-target lesions". Tumor response was determined by the local investigator every 8 weeks after start of the first trabedersen cycle during follow-up visits, irrespective of whether the patient was still on treatment or off treatment. The tumor assessment was based on Response Evaluation Criteria in Solid Tumors (RECIST 1.0) criteria. The categories of overall tumor response are as follows: (1) Complete response (CR): disappearance of all target and non-target lesions and normalization of tumor marker level; (2) Partial response (PR): at least 30% decrease in the sum of the longest diameter (LD) of target lesions (baseline sum LD as reference) and/or persistence of one or more non-target lesions and/or maintenance of tumor marker level above normal limits; (3) Stable disease (SD): less than 30% decrease or less than 20% increase in sum LD target lesions (smallest sum LD since treatment start as reference) and/or persistence of one or more non-target lesions and/or maintenance of tumor marker level above normal limits; (4) Progressive disease (PD) At least 20% increase in sum LD target lesions (smallest sum LD since treatment start as reference) and/or unequivocal progression of existing non-target lesions and/or appearance of one or more new lesions; and (5) Unknown.

Progression-Free Survival

Progression-free survival (PFS) was defined as the time from Day 1 until tumor progression or death from any cause. The date of progression was either the date of the image showing progression or the date of treatment termination in case one of the reasons for treatment termination was tumor progression (referring to clinical progression as assessed by the Investigator), whichever occurred first.

Overall Survival

Overall survival (OS) was defined as the time from Day 1 until death from any cause. All patients were followed for survival during the follow-up assessments every 8 weeks. The survival status was documented at the Final Visit (Day 29) and during the 8-weekly post-treatment follow-up assessments, and was continued to be collected after study closure until database lock or until the patient was lost to follow-up.

Pancreatic Cancer

There were 16 second line patients and 11 third line and beyond on the 4 days on and 10 days off regimen. The PFS/OS (progression free survival/overall survival ratio) of these second line patients in months were: 1.87/5.60 (N=6), 1.87/9.93 (N=11) and 2.72/11.80 (N=5) at increasing mean dose of 140 mg/m$^2$/day, 167 mg/m$^2$/day, and 196 mg/m$^2$/day, respectively. The OS of 9.93 and 11.80 are higher than the highest reported in the 65 trials reported in the literature during 1997-2015 (range=2.50-9.20/median=5.50). The corresponding PFS values were in line with reported literature (range=0.00-7.65/median=2.43). Consequently, the OS-PFS for trabedersen was vastly superior to that reported in the literature. This demonstrates that trabedersen was to make the tumor more sensitive to subsequent therapy. Trabedersen itself was not having an impact on the tumor (FIG. 1).

Figure 2:
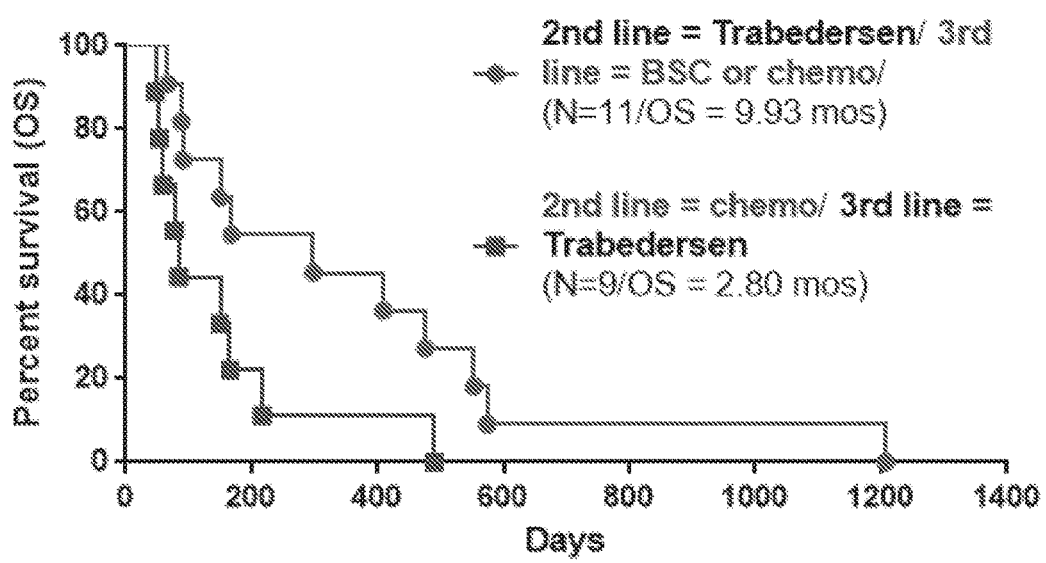
FIG. 2 depicts in accordance with various embodiments of the invention, that there is an increase in response to chemotherapy following trabedersen therapy as indicated by an increase in overall survival rate. This suggests that trabedersen sensitizes the tumor to chemotherapy.
Figure 3:
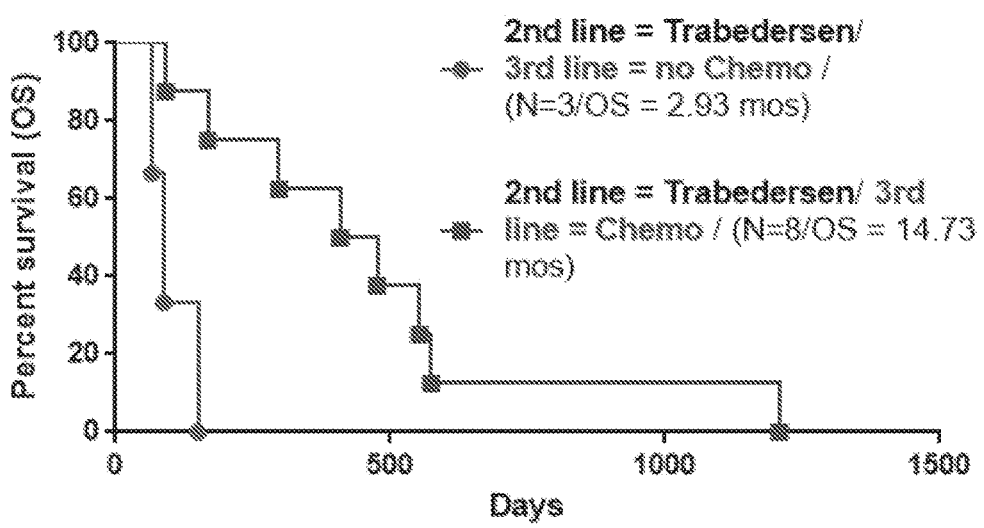
FIG. 3 depicts in accordance with various embodiments of the invention, that trabedersen alone does not have a significant effect on the tumor as indicated by a low overall survival rate but when trabedersen therapy is followed by chemotherapy, there is a significant increase in the overall survival rate. This suggests that trabedersen sensitizes the tumor to chemotherapy.

Chemotherapy on 2nd line followed with subsequent trabedersen 4/10 regimen as third line was ineffective compared to where patients were treated first with trabedersen on 2nd line followed with subsequent therapies with OS of 2.80 mos (N=9) versus 9.93 mos (N=11), p=0.046, Log-rank statistics. (FIG. 2). This again shows that trabedersen is sensitizing the tumor to subsequent treatments. The OS of this 4/10 cohort treated with subsequent chemotherapies was 14.7 versus 2.93 mos without subsequent chemotherapies, p=0.0023, Log-rank Statistics (FIG. 3). This again is showing that trabedersen is sensitizing the tumour to subsequent chemotherapies. The chemotherapies used for these patients are shown in Table 2 below.

TABLE 2

| Patient # | Regimen |
|---|---|
| 1019 | 5-Fluoronracil |
| 1019 | Folinic Acid |
| 1019 | Oxaliplatin |
| 1019 | Paclitaxel |
| 1019 | Mitomycin |
| 1019 | Capcitabine |
| 1022 | Gemcitabine |
| 1023 | Paclitaxel |
| 1023 | Fluorouracil |
| 1023 | Eloxatin |
| 1024 | 5-Fluorouracil |
| 1024 | Folinic Acid |
| 1024 | Oxaliplatin |
| 1029 | Capcitabine |
| 1029 | Erlotinib |
| 1029 | Radiotherapy |
| 1035 | Oxaliplatin |
| 1035 | 5-Fu |
| 1035 | Folinic Acid |
| 1035 | Paclitaxel |
| 1035 | Paclitaxel |
| 1035 | Paclitaxel |
| 1035 | Gemcitabine |
| 1040 | Gemcitabine |
| 1047 | Gemcitabine |
| 1047 | Erlotinib |

Trabedersen treatment was characterized by outstanding OS which was not supported by PFS. The effect was seen primarily when chemotherapies were used as third line after trabedersen treatment; OS benefit was not observed for the converse-chemotherapies used first followed by trabedersen. The data support the enhancement of subsequent chemotherapies following trabedersen treatment.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method for treating pancreatic cancer in a human subject in need thereof, comprising:
   sensitizing a pancreatic tumor in the subject to a chemotherapeutic agent, comprising sequentially administering to the subject an effective amount of Trabedersen for at least one cycle prior to administration of the chemotherapeutic agent; and
   subsequently administering an effective amount of the chemotherapeutic agent to the subject,
   wherein the chemotherapeutic agent is Paclitaxel, Dacarbazine or a combination thereof, and wherein Trabedersen sensitizes the tumor to Paclitaxel, Dacarbazine or a combination thereof, so as to treat pancreatic cancer in the subject.

2. The method of claim 1, wherein Trabedersen comprises a sequence 5'-CGGCATGTCTATTTTGTA-3' as set forth in SEQ ID NO: 1.

3. The method of claim 2, wherein Trabedersen does not reduce an $IC_{50}$ of the chemotherapeutic agent.

4. The method of claim 2, wherein the effective amount of Trabedersen is any one or more of 50-100 $mg/m^2$/day, 100-150 $mg/m^2$/day, 150-200 $mg/m^2$/day 200-250 $mg/m^2$/day, 250-300 $mg/m^2$/day, 300-350 $mg/m^2$/day, 350-400 $mg/m^2$/day, 400-450 $mg/m^2$/day, 450-500 $mg/m^2$/day or a combination thereof.

5. The method of claim 2, wherein the effective amount of Trabedersen is administered intravenously via continuous infusion, and the cycle is a 4 days on and 10 days off cycle.

6. The method of claim 5, wherein Trabedersen is administered for one, two, three, four or five cycles prior to administration of the chemotherapeutic agent.

7. The method of claim 1, wherein the Trabedersen is administered for two cycles.

* * * * *

SEQUENCE LISTING

<160> NUMBER OF SEQ ID NOS: 37

<210> SEQ ID NO 1
<211> LENGTH: 18
<212> TYPE: DNA
<213> ORGANISM: Artificial Sequence
<220> FEATURE:
<223> OTHER INFORMATION: Synthetically constructed human TGF-beta2
      antisense oligonucleotide

<400> SEQUENCE: 1
cggcatgtct attttgta                                                 18

<210> SEQ ID NO 2
<211> LENGTH: 5882
<212> TYPE: DNA
<213> ORGANISM: Homo sapiens
<220> FEATURE:
<223> OTHER INFORMATION: Homo sapiens transforming growth factor beta 2
      (TGFB2), transcript variant 2

<400> SEQUENCE: 2

| | | | | | |
|---|---|---|---|---|---|
| gtgatgttat | ctgctggcag | cagaaggttc | gctccgagcg | gagctccaga | agctcctgac | 60 |
| aagagaaaga | cagattgaga | tagagataga | aagagaaaga | gagaaagaga | cagcagagcg | 120 |
| agagcgcaag | tgaaagaggc | aggggagggg | gatggagaat | attagcctga | cggtctaggg | 180 |
| agtcatccag | gaacaaactg | aggggctgcc | cggctgcaga | caggaggaga | cagagaggat | 240 |
| ctattttagg | gtggcaagtg | cctacctacc | ctaagcgagc | aattccacgt | tggggagaag | 300 |
| ccagcagagg | ttgggaaagg | gtgggagtcc | aagggagccc | ctgcgcaacc | ccctcaggaa | 360 |
| taaaactccc | cagccagggt | gtcgcaaggg | ctgccgttgt | gatccgcagg | gggtgaacgc | 420 |
| aaccgcgacg | gctgatcgtc | tgtggctggg | ttggcgtttg | gagcaagaga | aggaggagca | 480 |
| ggagaaggag | ggagctggag | gctggaagcg | tttgcaagcg | gcggcggcag | caacgtggag | 540 |
| taaccaagcg | ggtcagcgcg | cgcccgccag | ggtgtaggcc | acggagcgca | gctcccagag | 600 |
| caggatccgc | gccgcctcag | cagcctctgc | ggccctgcg | gcacccgacc | gagtaccgag | 660 |
| cgccctgcga | agcgcaccct | cctcccgcg | gtgcgctggg | ctcgccccca | gcgcgcgcac | 720 |
| acgcacacac | acacacacac | acacacacgc | acgcacacac | gtgtgcgctt | ctctgctccg | 780 |
| gagctgctgc | tgctcctgct | ctcagcgccg | cagtggaagg | caggaccgaa | ccgctccttc | 840 |
| tttaaatata | taaatttcag | cccaggtcag | cctcggcggc | cccctcacc | gcgctcccgg | 900 |
| cgccctccc | gtcagttcgc | cagctgccag | ccccgggacc | ttttcatctc | ttcccttttg | 960 |
| gccggaggag | ccgagttcag | atccgccact | ccgcacccga | gactgacaca | ctgaactcca | 1020 |
| cttcctcctc | ttaaatttat | ttctacttaa | tagccactcg | tctcttttt | tccccatctc | 1080 |
| attgctccaa | gaattttttt | cttcttactc | gccaaagtca | gggttccctc | tgcccgtccc | 1140 |
| gtattaatat | ttccactttt | ggaactactg | gccttttctt | tttaaaggaa | ttcaagcagg | 1200 |
| atacgttttt | ctgttgggca | ttgactagat | tgtttgcaaa | agtttcgcat | caaaaacaac | 1260 |
| aacaacaaaa | aaccaaacaa | ctctccttga | tctatacttt | gagaattgtt | gatttctttt | 1320 |
| ttttattctg | acttttaaaa | acaacttttt | tttccacttt | tttaaaaaat | gcactactgt | 1380 |
| gtgctgagcg | cttttctgat | cctgcatctg | gtcacggtcg | cgctcagcct | gtctacctgc | 1440 |
| agcacactcg | atatggacca | gttcatgcgc | aagaggatcg | aggcgatccg | cggcagatc | 1500 |
| ctgagcaagc | tgaagctcac | cagtccccca | gaagactatc | ctgagcccga | ggaagtcccc | 1560 |
| ccggaggtga | tttccatcta | caacagcacc | agggacttgc | tccaggagaa | ggcgagccgg | 1620 |
| agggcggccg | cctgcgagcg | cgagaggagc | gacgaagagt | actacgccaa | ggaggtttac | 1680 |
| aaaatagaca | tgccgccctt | cttcccctcc | gaaaatgcca | tcccgcccac | tttctacaga | 1740 |
| ccctacttca | gaattgttcg | atttgacgtc | tcagcaatgg | agaagaatgc | ttccaatttg | 1800 |
| gtgaaagcag | agttcagagt | ctttcgtttg | cagaacccaa | agccagagt | gcctgaacaa | 1860 |
| cggattgagc | tatatcagat | tctcaagtcc | aaagatttaa | catctccaac | ccagcgctac | 1920 |
| atcgacagca | agttgtgaa | acaagagca | gaaggcgaat | ggctctcctt | cgatgtaact | 1980 |
| gatgctgttc | atgaatggct | tcaccataaa | gacaggaacc | tgggatttaa | aataagctta | 2040 |

-continued

```
cactgtccct gctgcactttt tgtaccatct aataattaca tcatcccaaa taaaagtgaa    2100
gaactagaag caagatttgc aggtattgat ggcacctcca catataccag tggtgatcag    2160
aaaactataa agtccactag gaaaaaaaac agtgggaaga ccccacatct cctgctaatg    2220
ttattgccct cctacagact tgagtcacaa cagaccaacc ggcggaagaa gcgtgctttg    2280
gatgcggcct attgctttag aaatgtgcag gataattgct gcctacgtcc actttacatt    2340
gatttcaaga gggatctagg gtggaaatgg atacacgaac ccaaagggta caatgccaac    2400
ttctgtgctg gagcatgccc gtatttatgg agttcagaca ctcagcacag cagggtcctg    2460
agcttatata ataccataaa tccagaagca tctgcttctc cttgctgcgt gtcccaagat    2520
ttagaacctc taaccattct ctactacatt ggcaaaacac ccaagattga acagctttct    2580
aatatgattg taaagtcttg caaatgcagc taaaattctt ggaaaagtgg caagaccaaa    2640
atgacaatga tgatgataat gatgatgacg acgacaacga tgatgcttgt aacaagaaaa    2700
cataagagag ccttggttca tcagtgttaa aaaattttttg aaaaggcggt actagttcag    2760
acactttgga agtttgtgtt ctgtttgtta aaactggcat ctgacacaaa aaagttgaa    2820 ggccttattc tacatttcac ctactttgta agtgagagag acaagaagca aattttttt    2880 aaagaaaaaa ataaacactg gaagaattta ttagtgttaa ttatgtgaac aacgacaaca    2940
acaacaacaa caacaaacag gaaaatccca ttaagtggag ttgctgtacg taccgttcct    3000
atcccgcgcc tcacttgatt tttctgtatt gctatgcaat aggcacccttt cccattctta    3060 ctcttagagt taacagtgag ttatttattg tgtgttacta tataatgaac gtttcattgc    3120
ccttggaaaa taaaacaggt gtataaagtg gagaccaaat actttgccag aaactcatgg    3180
atggcttaag gaacttgaac tcaaacgagc cagaaaaaaa gaggtcatat taatgggatg    3240
aaaacccaag tgagttatta tatgaccgag aaagtctgca ttaagataaa gaccctgaaa    3300
acacatgtta tgtatcagct gcctaaggaa gcttcttgta aggtccaaaa actaaaaaga    3360
ctgttaataa aagaaacttt cagtcagaat aagtctgtaa gtttttttt tctttttaa    3420 ttgtaaatgg ttcttttgtca gtttagtaaa ccagtgaaat gttgaaatgt tttgacatgt    3480
actggtcaaa cttcagacct taaaatattg ctgtatagct atgctatagg tttttccctt    3540
tgttttggta tatgtaacca tacctatatt attaaaatag atggatatag aagccagcat    3600
aattgaaaac acatctgcag atctcttttg caaactatta aatcaaaaca ttaactactt    3660
tatgtgtaat gtgtaaattt ttaccatatt tttatattc tgtaataatg tcaactatga    3720
tttagattga cttaaatttg ggctcttttt aatgatcact cacaaatgta tgtttctttt    3780
agctggccag tacttttgag taaagcccct atagtttgac ttgcactaca aatgcatttt    3840 tttttttaata acatttgccc tacttgtgct ttgtgtttct ttcattatta tgacataagc    3900
tacctgggtc cacttgtctt ttcttttttt tgtttcacag aaaagatggg ttcgagttca    3960
gtggtcttca tcttccaagc atcattacta accaagtcag acgttaacaa attttatgt     4020 taggaaaagg aggaatgtta tagatacata gaaaattgaa gtaaaatgtt ttcattttag    4080
caaggattta gggttctaac taaaactcag aatctttatt gagttaagaa aagtttctct    4140
accttggttt aatcaatatt tttgtaaaat cctattgtta ttacaaagag gacacttcat    4200
aggaaacatc tttttcttta gtcaggtttt taatattcag ggggaaattg aaagatatat    4260
attttagtcg attttttcaaa aggggaaaaa agtccaggtc agcataagtc attttgtgta    4320
tttcactgaa gttataaggt ttttataaat gttcttttgaa ggggaaaagg cacaagccaa    4380
tttttcctat gatcaaaaaa ttctttcttt cctctgagtg agagttatct atatctgagg    4440
```

```
ctaaagttta ccttgcttta ataaataatt tgccacatca ttgcagaaga ggtatcctca    4500
tgctggggtt aatagaatat gtcagtttat cacttgtcgc ttatttagct ttaaaataaa    4560
aattaatagg caaagcaatg gaatatttgc agtttcacct aaagagcagc ataaggaggc    4620
gggaatccaa agtgaagttg tttgatatgg tctacttctt ttttggaatt tcctgaccat    4680
taattaaaga attggatttg caagtttgaa aactggaaaa gcaagagatg ggatgccata    4740
atagtaaaca gccctgtgt tggatgtaac ccaatcccag atttgagtgt gtgttgatta     4800
tttttttgtc ttccactttt ctattatgtg taaatcactt ttatttctgc agacattttc    4860
ctctcagata ggatgacatt ttgttttgta ttattttgtc tttcctcatg aatgcactga    4920
taatatttta aatgctctat tttaagatct cttgaatctg ttttttttt ttttaatttg     4980 ggggttctgt aaggtcttta tttcccataa gtaaatattg ccatgggagg ggggtggagg    5040
tggcaaggaa ggggtgaagt gctagtatgc aagtgggcag caattatttt tgtgttaatc    5100
agcagtacaa tttgatcgtt ggcatggtta aaaaatggaa tataagatta gctgttttgt    5160
attttgatga ccaattacgc tgtatttaa cacgatgtat gtctgttttt gtggtgctct     5220
agtggtaaat aaattatttc gatgatatgt ggatgtcttt ttcctatcag taccatcatc    5280
gagtctagaa aacacctgtg atgcaataag actatctcaa gctggaaaag tcataccacc    5340
tttccgattg ccctctgtgc tttctccctt aaggacagtc acttcagaag tcatgcttta    5400
aagcacaaga gtcaggccat atccatcaag gatagaagaa atccctgtgc cgtcttttta    5460
ttcccttatt tattgctatt tggtaattgt ttgagattta gtttccatcc agcttgactg    5520
ccgaccagaa aaaatgcaga gagatgtttg caccatgctt tggctttctg gttctatgtt    5580
ctgccaacgc cagggccaaa agaactggtc tagacagtat cccctgtagc cccataactt    5640
ggatagttgc tgagccagcc agatataaca agagccacgt gctttctggg gttggttgtt    5700
tgggatcagc tacttgcctg tcagtttcac tggtaccact gcaccacaaa caaaaaaacc    5760
caccctattt cctccaattt ttttggctgc tacctacaag accagactcc tcaaacgagt    5820
tgccaatctc ttaataaata ggattaataa aaaagtaat tgtgactcaa aaaaaaaaa    5880 aa                                                                   5882

<210> SEQ ID NO 3
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 3
caaagtattt ggtctcc                                                   17

<210> SEQ ID NO 4
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 4
acctccttgg cgtagta                                                   17

<210> SEQ ID NO 5
```

-continued

```
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 5
acctccttgg cgtagta                                                      17

<210> SEQ ID NO 6
<211> LENGTH: 16
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 6
cctccttggc gtagta                                                       16

<210> SEQ ID NO 7
<211> LENGTH: 16
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 7
cctccttggc gtagta                                                       16

<210> SEQ ID NO 8
<211> LENGTH: 15
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 8
ctccttggcg tagta                                                        15

<210> SEQ ID NO 9
<211> LENGTH: 15
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 9
ctccttggcg tagta                                                        15

<210> SEQ ID NO 10
<211> LENGTH: 15
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 10
ctccttggcg tagta                                                        15

<210> SEQ ID NO 11
<211> LENGTH: 14
```

```
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 11
tccttggcgt agta                                                       14

<210> SEQ ID NO 12
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 12
cagaagttgg cat                                                        13

<210> SEQ ID NO 13
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 13
cagaagttgg cat                                                        13

<210> SEQ ID NO 14
<211> LENGTH: 12
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 14
ctgcccgcgg at                                                         12

<210> SEQ ID NO 15
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 15
tctgcccgcg gat                                                        13

<210> SEQ ID NO 16
<211> LENGTH: 14
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 16
tcgcgctcgc aggc                                                       14

<210> SEQ ID NO 17
<211> LENGTH: 15
<212> TYPE: DNA
```

```
<213> ORGANISM: Artificial Sequence
<220> FEATURE:
<223> OTHER INFORMATION: Synthetically constructed human TGF-beta
      antisense oligonucleotide

<400> SEQUENCE: 17
ggatctgccc gcgga                                                      15

<210> SEQ ID NO 18
<211> LENGTH: 15
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 18
ggatctgccc gcgga                                                      15

<210> SEQ ID NO 19
<211> LENGTH: 16
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 19
cgatcctctt gcgcat                                                     16

<210> SEQ ID NO 20
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 20
ggcgggatgg cat                                                        13

<210> SEQ ID NO 21
<211> LENGTH: 14
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 21
gaccagatgc agga                                                       14

<210> SEQ ID NO 22
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 22
cttgctcagg atctgcc                                                    17

<210> SEQ ID NO 23
<211> LENGTH: 13
<212> TYPE: DNA
<213> ORGANISM: Artificial Sequence
```

```
<220> FEATURE:
<223> OTHER INFORMATION: Synthetically constructed human TGF-beta
      antisense oligonucleotide

<400> SEQUENCE: 23
tctgtaggag ggc                                                        13

<210> SEQ ID NO 24
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 24
ccttaagcca tccatga                                                    17

<210> SEQ ID NO 25
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 25
tctgaactag taccgcc                                                    17

<210> SEQ ID NO 26
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 26
tactattatg gcatccc                                                    17

<210> SEQ ID NO 27
<211> LENGTH: 17
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 27
agcgtaattg gtcatca                                                    17

<210> SEQ ID NO 28
<211> LENGTH: 16
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 28
gcgaccgtga ccagat                                                     16

<210> SEQ ID NO 29
<211> LENGTH: 16
<212> TYPE: DNA
<213> ORGANISM: Artificial Sequence
<220> FEATURE:
```

```
<223> OTHER INFORMATION: Synthetically constructed human TGF-beta
      antisense oligonucleotide

<400> SEQUENCE: 29
aactagtacc gcctt                                                        16

<210> SEQ ID NO 30
<211> LENGTH: 14
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 30
gcgcgaccgt gacc                                                         14

<210> SEQ ID NO 31
<211> LENGTH: 14
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 31
accactagag cacc                                                         14

<210> SEQ ID NO 32
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 32
agcgcgaccg tga                                                          13

<210> SEQ ID NO 33
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 33
ggatcgcctc gat                                                          13

<210> SEQ ID NO 34
<211> LENGTH: 13
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 34
ctagtaccgc ctt                                                          13

<210> SEQ ID NO 35
<211> LENGTH: 12
<212> TYPE: DNA
<213> ORGANISM: Artificial Sequence
<220> FEATURE:
<223> OTHER INFORMATION: Synthetically constructed human TGF-beta
```

```
                antisense oligonucleotide

<400> SEQUENCE: 35
ccgcggatcg cc                                                          12

<210> SEQ ID NO 36
<211> LENGTH: 14
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 36
gaccgtgacc agat                                                        14

<210> SEQ ID NO 37
<211> LENGTH: 14
<212> TYPE: DNA
<213> ORGANISM: Artificial Sequence
<220> FEATURE:
<223> OTHER INFORMATION: Synthetically constructed human TGF-beta
      antisense oligonucleotide

<400> SEQUENCE: 37
gaccgtgacc agat                                                        14
```